US007655751B2

(12) United States Patent  
Itoh et al.

(10) Patent No.: US 7,655,751 B2
(45) Date of Patent: Feb. 2, 2010

(54) EPIDERMAL GROWTH FACTOR RECEPTOR-DERIVED PEPTIDES

(75) Inventors: Kyogo Itoh, Saga-ken (JP); Shigeki Shichijo, Kurume (JP)

(73) Assignee: Green Peptide Co., Ltd., Fukuoka (JP)

( * ) Notice: Subject to any disclaimer, the term of this patent is extended or adjusted under 35 U.S.C. 154(b) by 51 days.

(21) Appl. No.: 10/586,499

(22) PCT Filed: Jan. 21, 2005

(86) PCT No.: PCT/JP2005/000786

§ 371 (c)(1),
(2), (4) Date: Apr. 27, 2007

(87) PCT Pub. No.: WO2005/071075

PCT Pub. Date: Aug. 4, 2005

(65) Prior Publication Data

US 2008/0119399 A1 May 22, 2008

(30) Foreign Application Priority Data

Jan. 23, 2004 (JP) ............................. 2004-015676

(51) Int. Cl.
*A61K 38/00* (2006.01)
*C07K 2/00* (2006.01)
*C07K 4/00* (2006.01)
*C07K 5/00* (2006.01)
*C07K 14/00* (2006.01)
*C07K 16/00* (2006.01)
*C07K 17/00* (2006.01)
*A01N 37/18* (2006.01)

(52) U.S. Cl. .......................................... 530/300; 514/2
(58) Field of Classification Search ....................... None
See application file for complete search history.

(56) References Cited

FOREIGN PATENT DOCUMENTS

| WO | 00/18895 | 4/2000 |
| WO | 2004/067029 | 8/2004 |

OTHER PUBLICATIONS

Y. Lu et al., "Immunogene Therapy of Tumors with Vaccine Based on Xenogeneic Epidermal Growth Factor Receptor", The Journal of Immunology, vol. 170, No. 6, pp. 3162-3170, Mar. 15, 2003.
H. Takedatsu et al., "Expression of Epithelial Cancer-Related Antigens in Hematologic Malignancies Applicable for Peptide-Based Immunotherapy", Journal of Immunotherapy, vol. 27, pp. 289-297, 1997.
T. Mine et al., "Immunological Evaluation of CTL Precursor-Oriented Vaccines for Advanced Lung Cancer Patients", Cancer Science, vol. 94, No. 6, pp. 548-556, Jun. 6, 2003.
G. Gonzalez et al., "Epidermal Growth Factor-Based Cancer Vaccine for Non-Small-Cell Lung Cancer Therapy", Annals of Oncology, vol. 14, No. 3, pp. 461-466, Mar. 2003.
R. S.Herbst et al., "Targeting the Epidermal Growth Factor Receptor in Non-Small Cell Lung Cancer", Clinical Cancer Research, vol. 9, pp. 5813-5824, Dec. 1, 2003.
H. Shomura et al., "Identification of Epidermal Growth Factor Receptor-Derived Peptides Immunogenic for HLA-A2+ Cancer Patients", British Journal of Cancer, vol. 90, No. 8, pp. 1563-1571, Apr. 19, 2004.
T. Yamamoto et al., "Similarity of protein encoded by the human c-erb-B-2 gene to epidermal growth factor receptor", Nature, vol. 319, pp. 230-234, Jan. 16, 1986.
L. Coussens et al., "Tyrosine kinase receptor with extensive homology to EGF receptor shares chromosomal location with *neu* oncogene", Science, vol. 230, pp. 1132-1139, Dec. 1985.
D. S. Salomon et al., "Epidermal growth factor-related peptides and their receptors in human malignancies", Critical Reviews in Oncology/Hematology, vol. 19, pp. 183-232, 1995.
V. A. Miller et al., "Pilot trail of the epidermal growth factor receptor tyrosine kinase inhibitor gefitinib plus carboplatin and paclitaxel in patients with stage IIIB or IV non-small-cell lung cancer", Journal of Clinical Onocology, vol. 21, No. 11, pp. 2094-2100, Jun. 1, 2003.
M. Fukuoka et al., "Multi-institutional randomized phase II trial of gefitinib for previously treated patients with advanced non-small-cell lung cancer", Journal of Clinical Oncology, vol. 21, No. 12, pp. 2237-2246, Jun. 15, 2003.
G. E. Peoples et al., "Breast and ovarian cancer-specific cytotoxic T lymphocytes recognize the same HER2/neu-derived peptide", Proc. Natl. Acad. Sci., vol. 92, pp. 432-436, Jan. 1995.
B. Fisk et al., "Identification of an immunodominant peptide of HER-2/neu protooncogene recognized by ovarian tumor-specific cytotoxic T lymphocyte lines", J. Exp. Med., vol. 181, pp. 2109-2117, Jun. 1995.
I. Kawashima et al., "Identification of HLA-A3-restricted cytotoxic T lymphocyte epitopes from carcinoembryonic antigen and HER-2/neu by primary in vitro immunization with peptide-pulsed dendritic cells", Cancer Research, vol. 59, pp. 431-435, Jan. 15, 1999.
T. Okugawa et al., "A novel human HER2-derived peptide homologous to the mouse $K^d$-restricted tumor rejection antigen can induce HLA-A24-restricted cytotoxic T lymphocytes in ovarian cancer patients and healthy individuals", Eur. J. Immunol., vol. 30, pp. 3338-3346, 2000.
M. Noguchi et al., "Induction of cellular and humoral immune responses to tumor cells and peptides in HLA-A24 positive hormone-refractory prostate cancer patients by peptide vaccination", The Prostate, vol. 57, pp. 80-92, 2003.
Y. Sato et al., "Immunological evaluation of peptide vaccination for patients with gastric cancer based on pre-existing cellular response to peptide", Cancer Science, vol. 94, No. 9, pp. 802-808, Sep. 2003.
T. Mine et al., "Immunological evaluation of CTL precursor-oriented vaccines for advanced lung cancer patients", Cancer Sci., vol. 94, No. 6, pp. 548-556, Jun. 2003.

(Continued)

*Primary Examiner*—Robert Landsman
(74) *Attorney, Agent, or Firm*—Wenderoth, Lind & Ponack, L.L.P.

(57) ABSTRACT

The object of the invention is to provide an EGFR-derived peptide useful for EGFR-based immunotherapy.

The invention provides an EGFR-derived peptide capable of inducing both cellular and humoral immune responses and mutant peptide thereof and a polypeptide comprising said peptide, a nucleic acid molecule encoding the same, and a pharmaceutical composition comprising the same.

2 Claims, 12 Drawing Sheets

OTHER PUBLICATIONS

M. H. Parkar et al., "Expression of growth-factor receptors in normal and regenerating human periodontal cells", Archives of Oral Biology, vol. 46, pp. 275-284, 2001.

M. L. Disis et al., "High-titer HER-2/neu protein-specific antibody can be detected in patients with early-stage breast cancer", Journal of Clinical Oncology, vol. 15, No. 11, pp. 3363-3367, Nov. 1997.

E. Jager et al., "Induction of primary NY-ESO-1 immunity: CD8 + T lymphocyte and antibody responses in peptide-vaccinated patients with NY-ESO-1 + cancers", Proc. Natl. Acad. Sci., vol. 97, No. 22, pp. 12198-12203, Oct. 24, 2000.

S. Ohkouchi et al.,"Non-mutated tumor-rejection antigen peptides elicit type-I allergy in the majority of healthy individuals", Tissue Antigens, vol. 59, pp. 259-272, 2002.

N. Kawamoto et al., "IgG reactive to CTL-directed epitopes of self-antigens is either lacking or unbalanced in atopic dermatitis patients", Tissue Antigens, vol. 61, pp. 352-361, 2003.

T. Imanishi et al., "Allele and haplotype frequencies for HLA and complement loci in various ethnic groups", In: Proceedings of the Eleventh International Histocompatibility Workshop and Conference, pp. 1065-1220, Oxford University Press, Oxford, United Kingdom, 1992.

J. Dancey et al., "Issues and Progress with Protein Kinase Inhibitors for Cancer Treatment", Nature Rev. Drug Discovery, vol. 2, pp. 296-313, Apr. 2003.

Y. Yarden et al., "Untangling the ErbB signalling network", Nature Rev. Molecular Cell Biology, vol. 2, pp. 127-137, Feb. 2001.

J. Baselga et al., "Why the epidermal growth factor receptor? The rationale for cancer therapy", The Oncologist, vol. 7, Suppl. 4, pp. 2-8, 2002.

R. S. Herbst et al., "Selective oral epidermal growth factor receptor tyrosine kinase inhibitor ZD1839 is generally well-tolerated and has activity in non-small-cell lung cancer and other solid tumors: Results of a Phase I trial", Journal of Clinical Oncology, vol. 20, No. 18, pp. 3815-3825, Sep. 15, 2002.

Ch. Dittrich et al., "Phase I and pharmacokinetic study of BIBX 1382 BS, an epidermal growth factor receptor (EGFR) inhibitor, given in a continuous daily oral administration", European Journal of Cancer, vol. 38, pp. 1072-1080, 2002.

J. Mendelsohn et al., "Status of epidermal growth factor receptor antagonists in the biology and treatment of cancer", Journal of Clinical Oncology, vol. 21, No. 14, pp. 2787-2799, Jul. 15, 2003.

C. Meyer zum Buschenfelde et al., "The generation of both T killer and Th cell clones specific for the tumor-associated antigen HER2 using retrovirally transduced dendritic cells", The Journal of Immunology, vol. 167, pp. 1712-1719, 2001.

D. K. Moscatello et al., "A naturally occurring mutant human epidermal growth factor receptor as a target for peptide vaccine immunotherapy of tumors", Cancer Research, vol. 57, pp. 1419-1424, Apr. 15, 1997.

A. Ullrich et al., "Human epidermal growth factor receptor cDNA sequence and aberrant expression of the amplified gene in A431 epidermoid carcinoma cells", Nature, vol. 309, pp. 418-425, May 31, 1984.

A. T. Baron et al., "Monoclonal antibodies specific for peptide epitopes of the epidermal growth factor receptor's extracellular domain", Hybridoma, vol. 16, No. 3, pp. 259-271, 1997.

H. Shomura et al., "Identification of epidermal growth factor receptor-derived peptides recognised by both cellular and humoral immune responses in HLA-A24+ non-small cell lung cancer patients", European Journal of Cancer, vol. 40, pp. 1776-1786, 2004.

Canadian Office Action issued Apr. 3, 2009 in connection with Canadian Application No. 2,554,195 corresponding to the present U.S. application.

Yuji Sato et al., "Immunological evaluation of peptide vaccination for patients with gastric cancer based on pre-existing cellular response to peptide", Cancer Sci., vol. 94, No. 9, Sep. 2003, pp. 802-808.

SEQUENCE LISTING

<160> NUMBER OF SEQ ID NOS: 7

<210> SEQ ID NO 1
<211> LENGTH: 10
<212> TYPE: PRT
<213> ORGANISM: Artificial Sequence
<220> FEATURE:
<223> OTHER INFORMATION: EGFR-derived peptide at position 800-809.

<400> SEQUENCE: 1

Asp Tyr Val Arg Glu His Lys Asp Asn Ile
1               5                   10

<210> SEQ ID NO 2
<211> LENGTH: 9
<212> TYPE: PRT
<213> ORGANISM: Artificial Sequence
<220> FEATURE:
<223> OTHER INFORMATION: EGFR-derived peptide at position 124-132.

<400> SEQUENCE: 2

Asn Tyr Asp Ala Asn Lys Thr Gly Leu
1               5               9

<210> SEQ ID NO 3
<211> LENGTH: 9
<212> TYPE: PRT
<213> ORGANISM: Artificial Sequence
<220> FEATURE:
<223> OTHER INFORMATION: EGFR-derived peptide at position 54-62.

<400> SEQUENCE: 3

Met Phe Asn Asn Cys Glu Val Val Leu
1               5               9

<210> SEQ ID NO 4
<211> LENGTH: 10
<212> TYPE: PRT
<213> ORGANISM: Artificial Sequence
<220> FEATURE:
<223> OTHER INFORMATION: EGFR-derived peptide at position 479-488.

<400> SEQUENCE: 4

Lys Leu Phe Gly Thr Ser Gly Gln Lys Thr
1               5                   10

<210> SEQ ID NO 5
<211> LENGTH: 10
<212> TYPE: PRT
<213> ORGANISM: Artificial Sequence
<220> FEATURE:
<223> OTHER INFORMATION: EGFR-derived peptide at position 1138-1147.

<400> SEQUENCE: 5

Tyr Leu Asn Thr Val Gln Pro Thr Cys Val
1               5                   10

<210> SEQ ID NO 6
<211> LENGTH: 1210
<212> TYPE: PRT
<213> ORGANISM: Homo sapiens

<400> SEQUENCE: 6

Met Arg Pro Ser Gly Thr Ala Gly Ala Ala Leu Leu Ala Leu Leu Ala
1               5                   10                  15

```
Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
        35                  40                  45

Leu Ser Leu Gln Arg Met Phe Asn Asn Cys Glu Val Val Leu Gly Asn
    50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
        115                 120                 125

Lys Thr Gly Leu Lys Glu Leu Pro Met Arg Asn Leu Gln Glu Ile Leu
    130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Glu Asn Cys Gln
        195                 200                 205

Lys Leu Thr Lys Ile Ile Cys Ala Gln Gln Cys Ser Gly Arg Cys Arg
    210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
    290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
            340                 345                 350

Ala Thr Asn Ile Lys His Phe Lys Asn Cys Thr Ser Ile Ser Gly Asp
        355                 360                 365

Leu His Ile Leu Pro Val Ala Phe Arg Gly Asp Ser Phe Thr His Thr
    370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                405                 410                 415

Leu His Ala Phe Glu Asn Leu Glu Ile Ile Arg Gly Arg Thr Lys Gln
            420                 425                 430
```

```
His Gly Gln Phe Ser Leu Ala Val Val Ser Leu Asn Ile Thr Ser Leu
            435                 440                 445
Gly Leu Arg Ser Leu Lys Glu Ile Ser Asp Gly Asp Val Ile Ile Ser
        450                 455                 460
Gly Asn Lys Asn Leu Cys Tyr Ala Asn Thr Ile Asn Trp Lys Lys Leu
465                 470                 475                 480
Phe Gly Thr Ser Gly Gln Lys Thr Lys Ile Ile Ser Asn Arg Gly Glu
                485                 490                 495
Asn Ser Cys Lys Ala Thr Gly Gln Val Cys His Ala Leu Cys Ser Pro
                500                 505                 510
Glu Gly Cys Trp Gly Pro Glu Pro Arg Asp Cys Val Ser Cys Arg Asn
            515                 520                 525
Val Ser Arg Gly Arg Glu Cys Val Asp Lys Cys Lys Leu Leu Glu Gly
        530                 535                 540
Glu Pro Arg Glu Phe Val Glu Asn Ser Glu Cys Ile Gln Cys His Pro
545                 550                 555                 560
Glu Cys Leu Pro Gln Ala Met Asn Ile Thr Cys Thr Gly Arg Gly Pro
                565                 570                 575
Asp Asn Cys Ile Gln Cys Ala His Tyr Ile Asp Gly Pro His Cys Val
                580                 585                 590
Lys Thr Cys Pro Ala Gly Val Met Gly Glu Asn Asn Thr Leu Val Trp
            595                 600                 605
Lys Tyr Ala Asp Ala Gly His Val Cys His Leu Cys His Pro Asn Cys
        610                 615                 620
Thr Tyr Gly Cys Thr Gly Pro Gly Leu Glu Gly Cys Pro Thr Asn Gly
625                 630                 635                 640
Pro Lys Ile Pro Ser Ile Ala Thr Gly Met Val Gly Ala Leu Leu Leu
                645                 650                 655
Leu Leu Val Val Ala Leu Gly Ile Gly Leu Phe Met Arg Arg Arg His
                660                 665                 670
Ile Val Arg Lys Arg Thr Leu Arg Arg Leu Leu Gln Glu Arg Glu Leu
            675                 680                 685
Val Glu Pro Leu Thr Pro Ser Gly Glu Ala Pro Asn Gln Ala Leu Leu
        690                 695                 700
Arg Ile Leu Lys Glu Thr Glu Phe Lys Lys Ile Lys Val Leu Gly Ser
705                 710                 715                 720
Gly Ala Phe Gly Thr Val Tyr Lys Gly Leu Trp Ile Pro Glu Gly Glu
                725                 730                 735
Lys Val Lys Ile Pro Val Ala Ile Lys Glu Leu Arg Glu Ala Thr Ser
                740                 745                 750
Pro Lys Ala Asn Lys Glu Ile Leu Asp Glu Ala Tyr Val Met Ala Ser
            755                 760                 765
Val Asp Asn Pro His Val Cys Arg Leu Leu Gly Ile Cys Leu Thr Ser
        770                 775                 780
Thr Val Gln Leu Ile Thr Gln Leu Met Pro Phe Gly Cys Leu Leu Asp
785                 790                 795                 800
Tyr Val Arg Glu His Lys Asp Asn Ile Gly Ser Gln Tyr Leu Leu Asn
                805                 810                 815
Trp Cys Val Gln Ile Ala Lys Gly Met Asn Tyr Leu Glu Asp Arg Arg
                820                 825                 830
Leu Val His Arg Asp Leu Ala Ala Arg Asn Val Leu Val Lys Thr Pro
            835                 840                 845
```

-continued

Gln His Val Lys Ile Thr Asp Phe Gly Leu Ala Lys Leu Leu Gly Ala
            850                 855                 860

Glu Glu Lys Glu Tyr His Ala Glu Gly Gly Lys Val Pro Ile Lys Trp
865                 870                 875                 880

Met Ala Leu Glu Ser Ile Leu His Arg Ile Tyr Thr His Gln Ser Asp
            885                 890                 895

Val Trp Ser Tyr Gly Val Thr Val Trp Glu Leu Met Thr Phe Gly Ser
            900                 905                 910

Lys Pro Tyr Asp Gly Ile Pro Ala Ser Glu Ile Ser Ser Ile Leu Glu
            915                 920                 925

Lys Gly Glu Arg Leu Pro Gln Pro Pro Ile Cys Thr Ile Asp Val Tyr
            930                 935                 940

Met Ile Met Val Lys Cys Trp Met Ile Asp Ala Asp Ser Arg Pro Lys
945                 950                 955                 960

Phe Arg Glu Leu Ile Ile Glu Phe Ser Lys Met Ala Arg Asp Pro Gln
                965                 970                 975

Arg Tyr Leu Val Ile Gln Gly Asp Glu Arg Met His Leu Pro Ser Pro
            980                 985                 990

Thr Asp Ser Asn Phe Tyr Arg Ala Leu Met Asp Glu Asp Met Asp
            995                 1000                1005

Asp Val Val Asp Ala Asp Glu Tyr Leu Ile Pro Gln Gln Gly Phe Phe
            1010                1015                1020

Ser Ser Pro Ser Thr Ser Arg Thr Pro Leu Leu Ser Ser Leu Ser Ala
1025                1030                1035                1040

Thr Ser Asn Asn Ser Thr Val Ala Cys Ile Asp Arg Asn Gly Leu Gln
                1045                1050                1055

Ser Cys Pro Ile Lys Glu Asp Ser Phe Leu Gln Arg Tyr Ser Ser Asp
            1060                1065                1070

Pro Thr Gly Ala Leu Thr Glu Asp Ser Ile Asp Asp Thr Phe Leu Pro
            1075                1080                1085

Val Pro Glu Tyr Ile Asn Gln Ser Val Pro Lys Arg Pro Ala Gly Ser
            1090                1095                1100

Val Gln Asn Pro Val Tyr His Asn Gln Pro Leu Asn Pro Ala Pro Ser
1105                1110                1115                1120

Arg Asp Pro His Tyr Gln Asp Pro His Ser Thr Ala Val Gly Asn Pro
            1125                1130                1135

Glu Tyr Leu Asn Thr Val Gln Pro Thr Cys Val Asn Ser Thr Phe Asp
            1140                1145                1150

Ser Pro Ala His Trp Ala Gln Lys Gly Ser His Gln Ile Ser Leu Asp
            1155                1160                1165

Asn Pro Asp Tyr Gln Gln Asp Phe Phe Pro Lys Glu Ala Lys Pro Asn
            1170                1175                1180

Gly Ile Phe Lys Gly Ser Thr Ala Glu Asn Ala Glu Tyr Leu Arg Val
1185                1190                1195                1200

Ala Pro Gln Ser Ser Glu Phe Ile Gly Ala
            1205                1210

```
<210> SEQ ID NO 7
<211> LENGTH: 11
<212> TYPE: PRT
<213> ORGANISM: Artificial Sequence
<220> FEATURE:
<223> OTHER INFORMATION: HIV peptide with HLA-A24 binding motif

<400> SEQUENCE: 7

Arg Tyr Leu Arg Asp Gln Gln Leu Leu Gly Ile
 1               5                  10
```

EPIDERMAL GROWTH FACTOR RECEPTOR-DERIVED PEPTIDES

This application is a U.S. national stage of International Application No. PCT/JP2005/000786 filed Jan. 21, 2005.

BACKGROUND OF THE INVENTION

1. Field of the Invention

The invention relates to an EGFR-derived peptide useful for EGFR-based immunotherapy for cancer. In addition, the invention relates to a polypeptide comprising the EGFR-derived peptide capable of inducing both cellular and humoral immune responses and also a cancer vaccine containing said peptide.

2. Background of the Invention

Epithelial growth factor receptor (EGFR) plays an important role in epithelial biology and in many human malignancies (References 1-3). EGFR is a member of the receptor family comprising four, highly homologous proteins, HER2, HER3, and HER4 as well as EGFR. Those proteins in this family consist of an extracellular domain, a transmembrane domain, and an intracellular tyrosine kinase domain (Reference 20). Binding of the ligand such as epithelial growth factor (EGF) activates the intracellular tyrosine kinase domain to induce autophosphorylation of the receptor, which initiates the signaling cascade involved in cell proliferation and survival (Reference 20). The activation of EGFR highly involved in the processes of tumor proliferation and progression, including cell proliferation, inhibition of apoptosis, angiogenesis and metastasis (Reference 19). EGFR shows relatively high expression in approximately one-third of all types of epithelial cancers and the expression correlates with tumor progression, and therefore it is one of the most suitable targets in cancer therapy (References 21, 22).

As EGFR-targeted therapies, monoclonal antibodies which bind to the extracellular ligand binding site of the receptor and inhibitors for the intracellular tyrosine-kinase domain were intensively studied. Among them, a novel EGFR-tyrosine-kinase inhibitor ZD1839 is known to be effective for advanced non-small cell lung cancer (NSCLC) (References 4, 5).

It has been known that a living body has an immune system to eliminate tumor cells developed and that cytotoxic T lymphocyte (CTL) plays the central role in the system. CTL specifically recognizes an antigen presented on a tumor cell via a major histocompatibility complex (HLA in human) to kill the tumor cell. Taking advantage of the immune system for tumor cells, vaccine therapies, which include immunization of a body with epitope peptides of tumor antigens, have been attempted to potentiate the cytotoxicity against tumor cells.

Epitope peptides of HER2/neu, a member of the receptor family of EGFR, capable of inducing HLA-class I-restricted CTL were reported in the past decade (References 6-9). The inventers of the present invention previously reported that some CTL-directed peptides derived from non-mutated proliferation-related proteins had the ability to elicit both cellular and humoral immune responses in vivo in clinical studies (References 10-12). Further, levels of anti-peptide Abs in post-vaccination sera were well correlated with overall survival of advanced lung cancer patients who received peptide vaccination (Reference 12). In addition, there is a line of evidence for higher immunogenicity of a peptide capable of inducing both cellular and humoral immune responses (References 13-15), which can be expected to have more potent therapeutic activity.

The CTL epitope peptide of EGFR may be useful in cancer therapies in a different way from existing compounds, because it can be used as a peptide vaccine in EGFR-targeted therapies for cancer patients with tumors overexpressing EGFR. So far, however, there is no information about CTL epitopes of EGFR.

REFERENCES

1. Yamamoto, T., Ikawa, S., Akiyama, T., Semba, K., Nomura, N., Miyajima, N., Saito, T., and Toyoshima, K. Similarity of protein encoded by the human c-erb-B-2 gene to epidermal growth factor receptor. Nature, 319:230-234, 1986.
2. Coussens, L., Yang-Feng, T. L., Liao, Y.-C., Chen, E., Gray, A., McGrath, J., Seeburg, P. H., Libermann, T. A., Schlessinger, J., Francke, U., Levinson, A., and Ullrich, A. Tyrosine kinase receptor with extensive homology to EGF receptor shares chromosomal location neu oncogene. Science, 230:1132-1139, 1985.
3. Salomon, D. S., Brandt, R., Ciardiello, F., and Normanno, N. Epidermal growth factor-related peptides and their receptors in human malignancies. Crit. Rev. Oncol. Hematol., 19:183-232, 1995.
4. Miller, V. A., Johnson, D. H., Krug, L. M., Pizzo, B., Tyson, L., Perez, W., Krozely, P., Sandler, A., Carbone, D., Heelan, R. T., Kris, M G., Smith, R., and Ochs, J. Pilot trial of the epidermal growth factor receptor tyrosine kinase inhibitor gefitinib plus carboplatin and paclitaxel in patients with stage IIIB or IV non-small-cell lung cancer. J. Clin. Oncol., 21:2094-2100, 2003.
5. Fukuoka, M., Yano, S., Giaccone, G., Tamura, T., Nakagawa, K., Douillard, J. Y., Nishiwaki, Y., Vansteenkiste, J., Kudoh, S., Rischin, D., Eek, R., Horai, T., Noda, K., Takata, I., Smit, E., Averbuch, S., Macleod, A., Feyereislova, A., Dong, R. P., and Baselga, J. Multi-institutional randomized phase II trial of gefitinib for previously treated patients with advanced non-small-cell lung cancer. J. Clin. Oncol., 21:2237-2246, 2003.
6. Peoples, G. E., Goedegebuure, P. S., Smith, R., Linehan, D. C., Yoshino, I., and Eberlein, T. J. Breast and ovarian cancer-specific cytotoxic T lymphocytes recognize the same HER2/neu-derived peptide. Proc. Natl. Acad. Sci. USA, 92:432-436, 1995.
7. Fisk, B., Blevins, T. L., Wharton, J. T., and Ioannides, C. G. Identification of an immunodominant peptide of HER-2/neu protooncogene recognized by ovarian tumor-specific cytotoxic T lymphocyte lines. J. Exp. Med., 181:2109-2717
8. Kawashima, I., Tsai, V., Southwood, S., Takesako, K., Sette, A., and Celis, E. Identification of HLA-A3-restricted cytotoxic T lymphocyte epitopes from carcinoembryonic antigen and HER-2/neu by primary in vitro immuneization with peptide-pulsed dendritic cells. Cancer, Res., 59:431-435, 1999.
9. Okugawa, T., Ikuta, Y., Takahashi, Y., Obata, H., Tanida, K., Watanabe, M., Imai, S., Furugen, R., Nagata, Y., Toyoda, N., and Shuku, H. A novel human HER2-derived peptide homologous to the mouse Kd-restricted tumor rejection antigen can induce HLA-A24-restricted cytotoxic T lymphocytes in ovarian cancer patients and healthy individuals. Eur. J. Immunol., 30:3338-3346, 2000.
10. Noguchi, M., Kobayashi, K., Suetsugu, N., Tomiyasu, K., Suekane, S., Yamada, A., Itoh, K. and Noda, S. Induction Of Cellular And Humoral Immune Responses To Tumor Cells And Peptides In HLA-A24 Positive Hormone-RefractoryProstate Cancer Patients By Peptide Vaccination. Prostate, in press, 2003.

11. Sato, Y., Shomura, H., Maeda, Y., Mine, T., Une, Y., Akasaka, Y., Kondo, M., Takahashi, S., Shinohara, T., Katagiri, K., Sato, S., Okada, S., Matsui, K., Yamada, A., Yamana, H., Itoh, K., and Todo, S. Immunological evaluation of peptide vaccination for patients with gastric cancer based on pre-existing cellular response to peptide. Cancer Sci., in press, 2003.
12. Mine, T., Gouhara, R., Hida, N., Imai, N., Azuma, K., Rikimaru, T., Katagiri, K., Nishikori, M., Sukehiro, A., Nakagawa, M., Yamada, A., Aizawa, H., Shirouzu, K., Itoh, K., and Yamana, H. Immunological evaluation of CTL precursor-oriented vaccines for advanced lung cancer patients. Cancer Sci., 94:548-556, 2003.
13. Parkar, M. H., Kuru, L., Giouzeli, M., and Olsen, I. Expression of growth-factor receptors in normal and regenerating human periodontal cells. Arch. Oral. Biol., 46:275-284, 2001.
14. Disis, M. L., Pupa, S. M., Gralow, J. R., Dittadi, R., Menard, S., and Cheever, M. A. High-titer HER-2/neu protein-specific antibody can be detected in patients with early-stage breast cancer. J. Clin. Oncol., 11:3362-7.
15. Jager, E., Gnjatic, S., Nagata, Y., Stockert, E., Jager, D., Karbach J, Neumann, A., Rieckenberg, J., Chen, Y. T., Ritter, G., Hoffman, E., Arand, M., Old, L. J., and Knuth, A. Induction of primary NY-ESO-1 immunity: CD8+ T lymphocyte and antibody responses in peptide-vaccinated patients with NY-ESO-1+ cancers. Proc. Natl. Acad. Sci. USA, 97:12198-12203, 2000.
16. Ohkouchi, S., Yamada, A., Imai, N., Mine, T., Harada, K., Shichijo, S., Maeda, Y., Saijo, Y., Nukiwa, T., and Itoh, K. Non-mutated tumor-rejection antigen peptides elicit type-I allergy in the majority of healthy individuals. Tissue Antigens, 59:259-272, 2002.
17. Kawamoto, N., Yamada, A., Ohkouchi, S., Maeda, T., Tanaka, S., Hashimoto, T., Saijo, Y., Saijo, S., Nukiwa, T., Shichijo, S., Aizawa, H., and Itoh, K. IgG reactive to CTL-directed epitopes of self-antigens is enter lacking or unbalanced in atopic dermatitis patients. Tissue Antigen, 61:352-361, 2003.
18. Imanishi, T., Akaza, T., Kimura, A., Tokunaga, K., and Gojobori, T. Allele and haplotype frequencies for HLA and complement loci in various ethnic groups. In: Proceedings of the Eleventh International Histocompatibility Workshop and Conference. pp. 1065-1220. Oxford, United Kingdom: Oxford University Press, 1992.
19. Dancey, J. & Sausville, E. A. Issues and progress with protein kinase inhibitors for the treatment of cancer. Nature Rev. Drug Discov. 2,296-313 (2003).
20. Yarden, Y. & Sliwkowski, M. X. Untangling the ErbB signalling network. Nature Rev. Mol. Cell Biol. 2, 127-137 (2001).
21. Baselga, J. Why the epidermal growth factor receptor? The rationale for cancer therapy. The Oncologist 7(S4), 2-8 (2002).
22. Salomon, D. S. et al. Epidermal growth factor-related peptides and their receptors in human malignancies. Crit. Rev. Oncol. Hematol. 19, 183-232 (1995).
23. Herbst R S, Maddox A M, Rothenberg M L, Small E J, Rubin E H, Baselga J, Rojo F, Hong W K, Swaisland H, Averbuch S D, Ochs J, LoRusso P M (2002) Selective oral epidermal growth factor receptor tyrosine kinase inhibitor ZD1839 is generally well-tolerated and has activity in non-small-cell lung cancer and other solid tumor: results of a phase I trial. J Clin Oncol 20: 3815-3825.
24. Dittrich Ch, Greim G, Borner M, Weigang-Kohler K, Huisman H, Amelsberg A, Ehret A, Wanders J, Hanauske A, Fumoleau P (2002) Phase I and pharmacokinetic study of BIBX 1382 BS, an epidermal growth factor receptor (EGFR) inhibitor, given in a continuous daily oral administration. Eur J Cancer 38: 1072-1080.
25. Mendelsohn J, Baselga J (2003) Status of epidermal growth factor receptor antagonista in the biology and treatment of cancer. J Clin Oncol 21: 2787-2799.

DISCLOSURE OF THE INVENTION

Problem to be Solved by the Invention

An object of the invention is to provide a peptide which is useful as a cancer vaccine in view of the development of EGFR-based cancer therapy.

Means of Solving the Problem

To identify EGFR-derived peptides capable of inducing humoral immune response, the inventors first investigated whether specific antibodies against EGFR-derived peptides are present in sera of NSCLC patients and healthy donors (HDs). Those peptides could induce CTLs which specifically kill EGFR-expressing tumor cells, and thus the present invention was accomplished.

Accordingly, the invention provides:
(1) an EGFR-derived peptide or mutant peptide thereof which is capable of inducing a CTL and an antibody specific for said peptide, preferably the peptide which is an HLA-A24- or HLA-A2-restricted peptide;
(2) the peptide of (1), wherein the EGFR-derived peptide consists of at least 8 consecutive amino acid residues derived from the amino acid sequence of $EGFR_{800-809}$, $EGFR_{124-132}$, $EGFR_{54-62}$, $EGFR_{479-488}$ or $EGFR_{1138-1147}$;
(3) a polypeptide consisting of 8 to 50 amino acid residues, which comprises the peptide of (1) or (2) and is capable of inducing a CTL and an antibody specific for said peptide;
(4) a nucleic acid molecule encoding the peptide of (1) or (2) or a polypeptide comprising said peptide;
(5) a vector comprising the nucleic acid molecule of (4);
(6) a pharmaceutical composition comprising the peptide of (1) or (2), the polypeptide of (3), or the nucleic acid molecule of (4) for inducing a CTL and an antibody specific for said peptide;
(7) the pharmaceutical composition of (6), which is used as a cancer vaccine;
(8) an EGFR-reactive CTL which recognizes a complex between the peptide of (1) or
(2) or the polypeptide of (3) and an HLA molecule;
(9) a method of inducing an EGFR-reactive CTL using the peptide of (1) or (2) or the polypeptide of (3);
(10) an antibody which specifically recognizes the peptide of (1) or (2) or the polypeptide of (3).

BEST MODE FOR CARRYING OUT THE INVENTION

Peptide and Polypeptide

Figure 1:
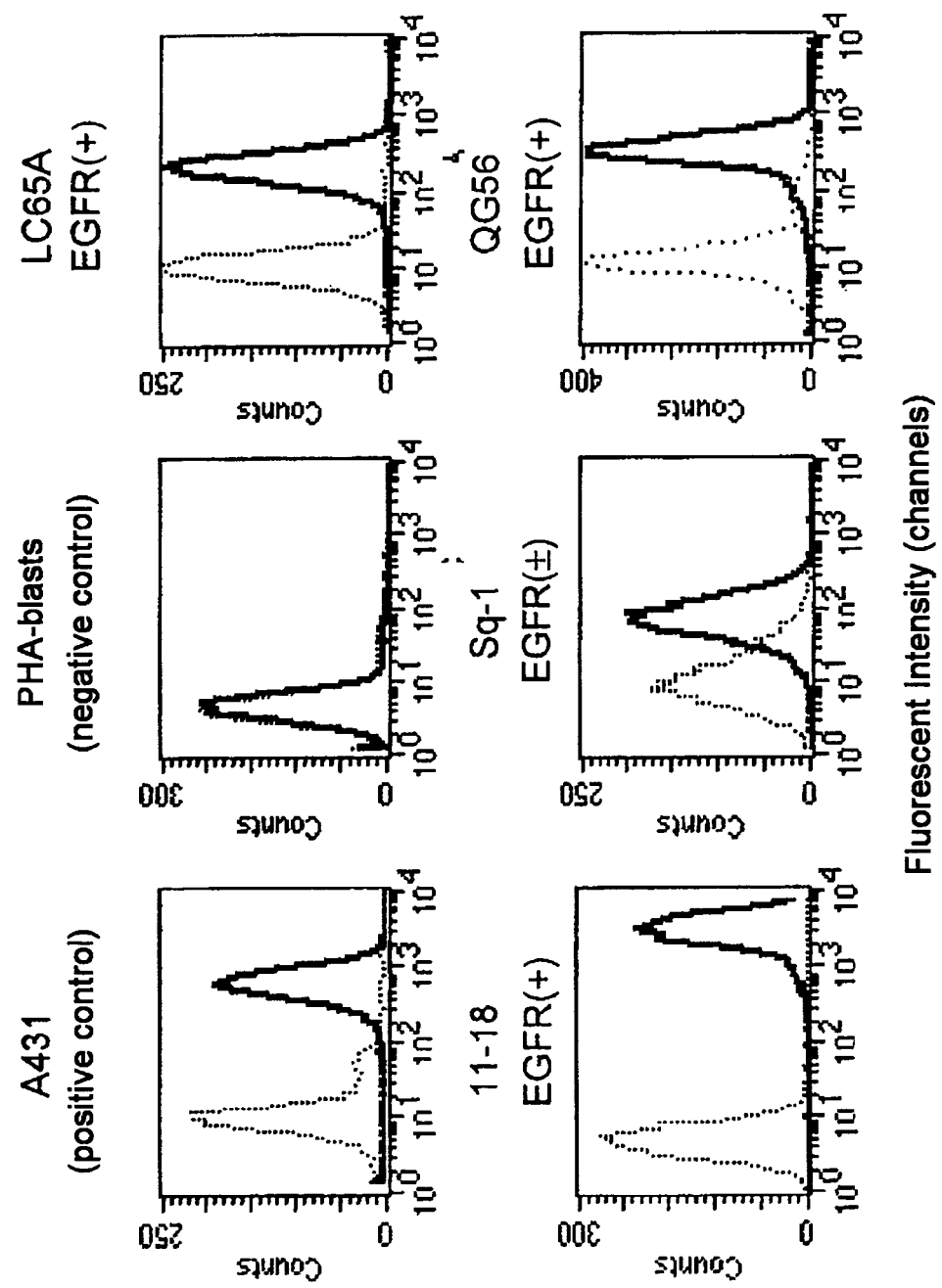
FIG. 1 shows the representative histograms demonstrating EGFR expression on tumor cells analyzed by a flow cytometry assay. The dot line shows the result with the second antibody (FITC-bound control antibody) only, and the black line shows that with an anti-EGFR monoclonal antibody plus the second antibody.

The EGFR-derived peptide of the invention is capable of inducing both cellular and humoral immune responses and has a high immunogenicity. The inventers have reported that IgGs reactive against CTL epitope peptides were often detected in pre-vaccination sera of cancer patients and HDs (References 10-12, 16, 17). Further, some CTL-directed peptides have the ability to elicit both cellular and humoral immune responses in vivo in the phase I clinical studies, and the levels of anti-peptide Ab in post-vaccination sera well correlated with over-all survival of advanced cancer patients who received peptide vaccination (References 11,12). In addition, the adverse events found in a number of clinical studies of EGFR-targeted cancer therapies, such as acne-like eruption and diarrhea (References 23, 24, 25), have not been observed in the phase I clinical studies of vaccine therapy performed by the inventers with EGFR-derived peptides. Those results indicate that the peptides of the invention are useful as cancer vaccines in EGFR-targeted cancer therapy.

Preferably, the peptide of the invention is a HLA-A24- or HLA-A2-restricted peptide. The peptide capable of inducing both cellular and humoral immune responses is, for example, EGFR$_{800-809}$ (SEQ ID NO. 1), EGFR$_{124-132}$ (SEQ ID NO. 2), EGFR$_{54-62}$ (SEQ ID NO. 3), EGFR$_{479-488}$ (SEQ ID NO. 4) or EGFR$_{1138-1147}$ (SEQ ID NO. 5). The whole amino acid sequence of EGFR is deposited in GeneBank with the deposition number of CAA25240 (SEQ ID NO. 6).

Other EGFR-derived peptides capable of inducing their specific CTLs and antibodies can be easily identified and selected according to the working examples hereinafter. Considering the activity of immune response induction, EGFR$_{43-51}$ and EGFR$_{943-952}$ are also potential peptides of the invention.

The invention also includes the mutant peptide of any one of the above peptides of SEQ ID NOS. 1 to 5, wherein the mutant peptide has the CTL- and antibody-inducing activities equivalent to those of its original peptide. The alteration may be deletion, substitution, addition, or insertion of one or more of amino acids in the EGFR-derived peptide of the invention, and the methods for such alteration are well known in the art. The mutant peptide can be selected according to the recognition by CTL. The number of amino acid residues of the mutant peptide may be that sufficient to be presented on an antigen presenting cell and to work as a CTL-recognizing epitope, and at least 8, preferably at least 9 and more preferably 9 or 10.

The invention further provides the polypeptide comprising the EGFR-derived peptide of the invention or mutant peptide thereof, wherein the polypeptide is capable of inducing the specific CTL and antibody. The polypeptide generally has the length of amino acid residues of 8-50, preferably 8-30, more preferably 9-10 or 8-10. The polypeptide preferably comprises the EGFR-derived peptide selected from EGFR$_{800-809}$ (SEQ ID NO. 1), EGFR$_{124-132}$ (SEQ ID NO. 2), EGFR$_{54-62}$ (SEQ ID NO. 3), EGFR$_{479-488}$ (SEQ ID NO. 4) and EGFR$_{1138-1147}$ (SEQ ID NO. 5).

The peptide and polypeptide of the invention may be modified on their constituent amino acids or carboxyl groups to the extent that their functions are not significantly damaged.

The peptide and polypeptide of the invention may be synthesized by any of usual methods known in peptide chemistry.

Nucleic Acid Molecule

The nucleic acid molecule of the invention includes a single-stranded polynucleotide (including complementary strand thereof) and a double-stranded polynucleotide encoding the amino acid sequence of the EGFR-derived peptide of the invention, the mutant peptide thereof or the polypeptide comprising the same. The nucleic acid molecule of the invention may be DNA or RNA. The peptide having the amino acid sequence encoded by the nucleic acid molecule can be recognized by CTL to activate the CTL and function as a tumor antigen.

In addition, the nucleic acid molecule of the invention may be the polynucleotide or complementary strand thereof consisting of at least 24 bases corresponding to the coding region for the peptide of the invention. The polynucleotide can be selected, for example, by checking the peptide expressed from the polynucleotide by any of known protein expression systems.

Antibody

The antibody of the invention specifically recognizes a peptide consisting of at least 5 consecutive amino acid residues which is derived from any of the amino acid sequences of the EGFR-derived peptides or the polypeptides of the invention. The antibody can be prepared using its epitope peptide which consists of at least 5, preferably at least 8-10 amino acids. The present invention encompasses said peptide consisting of at least 5 amino acids and also the nucleic acid molecule encoding said peptide. The amino acid sequence of the epitope is not necessarily identical to the amino acid sequence of any of SEQ ID NOS. 1 to 5, but the peptide consisting of the amino acid sequence has to be recognized by CTL.

The antibody of the invention can be prepared by immunizing a suitable animal, such as mouse, rat, rabbit, goat and the like, with the epitope peptide of EGFR or that of an EGFR-derived peptide or polypeptide, alone or in conjunction with any suitable carrier, in the absence or presence of adjuvant, to induce the antibody production. The polyclonal antibodies obtained can be collected from the serum of the animal by any of known methods.

Further, a monoclonal antibody can be prepared by fusing the antibody-producing cells collected from the immunized animal as above to tumor cells which replicate endlessly. This method is well known in the art.

Those polyclonal and monoclonal antibodies are useful for purification or as a reagent, a labeling marker, and the like. As far as we examined, anti-EGFR peptide IgGs fail to directly inhibit tumor growth in vitro and to elicit antibody-dependent cell-mediated cytotoxicity against tumor cells (data is not shown herein). The anti-EGFR peptide IgG, therefore, may not act on tumor cells. The anti-peptide IgG, however, may facilitate infiltration of immunocompetent cells into tumor sites through induction of inflammatory reactions around tumor sites; inflammatory reactions around tumors were observed at the time of surgery (radical prostatectomy) for prostate cancer patients who had received the peptide vaccination prior to the prostatectomy; in the same patients, increased levels of IgG reactive to the vaccinated peptides were observed in the sera of post-vaccination but pre-surgery (Noguchi et al., unpublished results). The antibody of the invention is thereby assumed to have a potential to help the anti-tumor activity. Moreover, IgGs reactive to CTL epitope peptides were either lacking or unbalanced in sera of patients with atopic disease (Reference 17). These results suggest that IgGs to CTL peptides are involved in host-defense against various diseases, although underlying mechanism of anti-tumor immune responses in cancer patients is presently unclear.

Pharmaceutical Composition

The pharmaceutical composition of the invention can be prepared with the EGFR-derived peptide or polypeptide of the invention, the nucleic acid molecule encoding the same, the vector prepared based on the sequence of said nucleic acid molecule, or the antibody of the invention, or combination thereof.

Particularly, the EGFR-derived peptide of the invention or mutant peptide thereof and the polypeptide comprising said peptide can be used as cancer vaccines.

The pharmaceutical composition of the invention is useful as a cancer vaccine in EGFR-based immunotherapy, and it can be used for treating epithelial cancer, such as non-small-cell lung cancer, ovarian cancer, prostate cancer, breast cancer, gastric cancer, GIST tumor (gastrointestinal stromal tumor), pancreas cancer and the like. "EGFR-targeted therapy" is herein used in a broad sense and includes not only therapies using antibodies but also those using antagonists of the ligand (in this case EGFR) or inhibitors of signal transducers (including receptors and any component of receptor-meditated signal transductions, as EGFR is a receptor of cell growth factor EGF). In contrast, "EGFR-based immunotherapy" is used in a narrower sense, wherein EGFR is the target molecule of the antibody or T cells.

For the pharmaceutical composition of the invention, combinations of more than one peptide are preferably used, although a single peptide is still useful as a cancer vaccine. This is because CTLs of a cancer patient consist of groups of cells each recognizing different tumor antigens and therefore such combination are expected to be more effective than a single peptide as cancer vaccines. The peptides of the invention may be combined each other.

The peptide or polypeptide of the invention as a cancer vaccine may be used in the presence or absence of any suitable adjuvant, alone or as a mixture or conjugate with any pharmaceutically acceptable carrier. The carrier is not limited as long as it has no adverse effect on a human body, and the examples are cellulose, amino acid polymers, and albumin.

The dosage form may be selected from those well known for peptide drugs. The dose is 0.01-100 mg/day/adult human, preferably 0.1-10 mg/day/adult human, although it may vary depending on the recognition by CTL, and it may be administered once in several days or several months.

The pharmaceutical composition of the invention may comprise an appropriate vector which includes the nucleic acid sequence encoding the peptide of the invention. The composition can be used in vivo or ex vivo. The vector may be retrovirus, adenovirus or vaccinia virus, and preferably retrovirus. The dose is 0.1 μg-100 mg/day/adult human, preferably 1 μg-50 mg/day/adult human, although it may vary depending on the recognition by CTL. It may be administered once in several days or several months.

Method for Induction of CTL

The EGFR-reactive CTL is induced, for example, with the peptide of the invention from peripheral blood cells (PBMCs) of a NSCLC patient.

In brief, PBMCs isolated from a NSCLC patient are incubated with antigen presenting cells (APCs) pulsed with the peptide of the invention to induce CTLs, and the induction is evaluated by IFN-γ production of the cells. The activity of the CTLs induced can be confirmed by $^{51}$Cr release assay which indicates the tumor cytotoxicity of the cells The above method may be useful for adoptive immunotherapy in which antigen-specific CTLs induced in vitro are returned to the patient to kill his tumor cells.

The present invention is further described by the following Examples, but not limited by them in any sense.

EXAMPLES

Example 1

Immunogenic EGFR-derived Peptides

A. Identification of the Activity of Inducing Humoral Immune Response

This study was made to determine whether Immunogloblin G (IgG)s reactive to EGFR-derived peptides could be detected in sera of 13 NSCL cancer patients and 11 HDs.

The following 18 EGFR-derived peptides with HLA-A24 binding motif were purchased from BioSynthesis (Lewisville, Tex.). Those peptides correspond to positions 43-51, 54-62, 68-76, 73-82, 111-119, 124-132, 269-277, 625-633, 722-730, 800-809, 812-821, 899-907, 899-908, 943-952, 960-969, 1015-1023, 1015-1024, and 1068-1077 of EGFR, respectively. An HIV peptide with HLA-A24 binding motif (RYLRDQQLLGI SEQ ID NO: 7) was also provided as a negative control.

After written informed consent was obtained, sera and peripheral blood mononuclear cells (PBMCs) were collected from NSCLC patients and HDs at Kurume University Hospital, and the sera and PBMCs were cryopreserved at −80° C. and −196° C. until use, respectively. All subjects were free from HIV infection. Expression of HLA-class I antigens on these PBMCs was serologically defined by the conventional methods as reported previously (Reference 10).

Peptide-specific IgG levels in sera were measured by an enzyme-linked immunosorbent assay (ELISA) as reported previously (Reference 11). Briefly, serum samples were serially diluted with 0.05% Tween 20-Block Ace (Yukijirushi nyugyo, Hokkaido, Japan), and 100 μl/well of the diluted serum were added to the peptide (20 μg/well)-immobilized Nunc Covalink plates (Fisher Scientific, Pittsburgh, Pa.). Anti-peptide Abs were detected with rabbit anti-human IgG (γ-chain-specific) (DAKO, Glostrp, Denmark). For determining the limit of sensitivity of ELISA, sera from 10 healthy donors (HIV-negative) were measured for their reactivity to an HIV peptide by the assays. The mean ±SD of absorbance (A) indicated at 0.020±0.02, and the mean +SD value (0.04) was then determined as the cut-off value.

Figure 2:
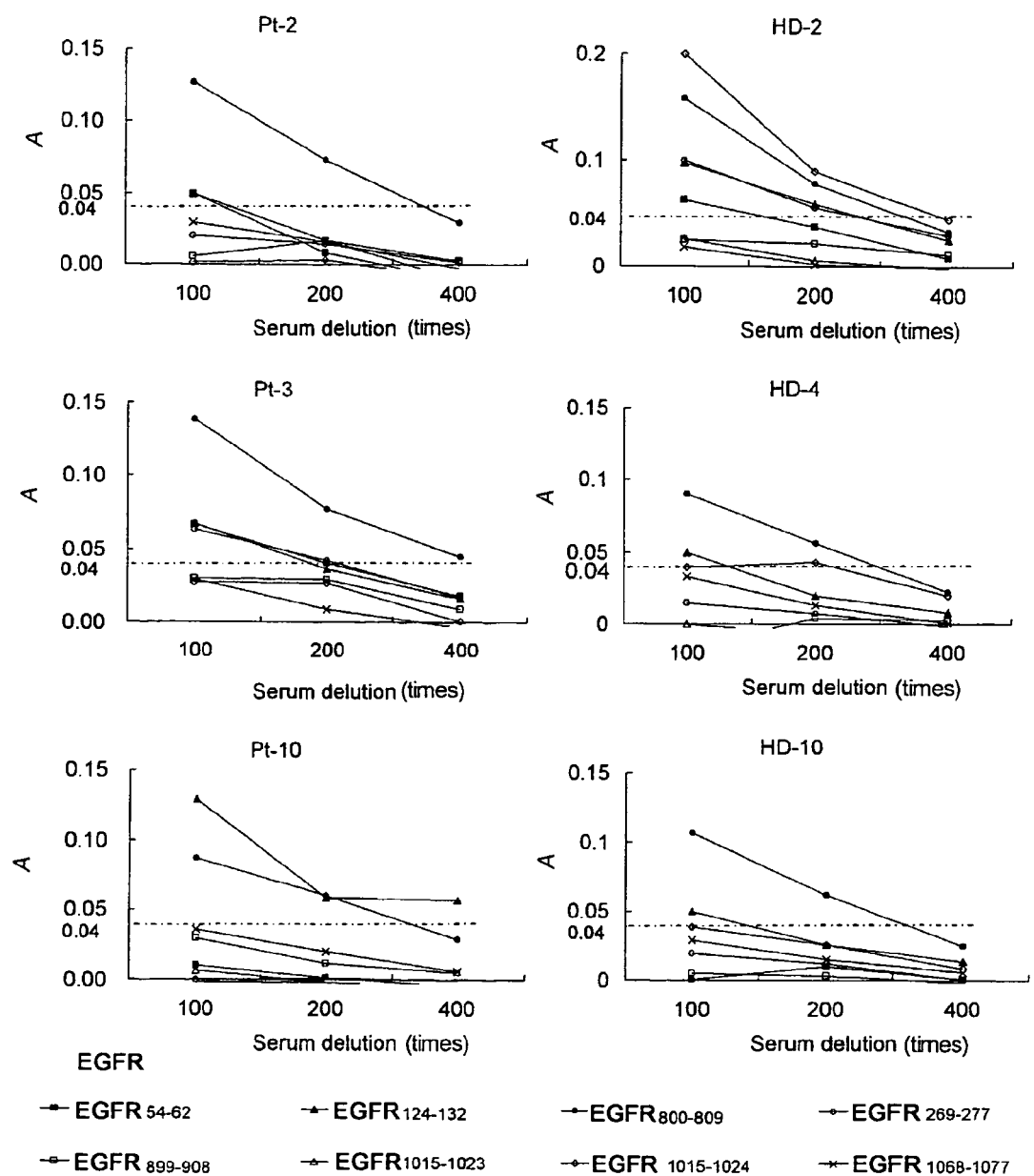
FIG. 2 shows the detection of the anti-peptide IgGs in the serum samples.

FIG. 2 shows the representative results of three NSCLC patients (Pts. 2, 3, and 10) and three HDs (HDs 2, 4, and 10). The A value against the HIV peptide used as a negative control was subtracted from the data.

Summary of the results on 11 peptides, to which sera of some subjects showed positive responses, is given in Table 1.

TABLE 1

Humoral responses to the EGFR peptides

| Subjects | HLA | EGFR899-908 | EGFR1015-1024 | EGFR800-809 | EGFR269-277 | EGFR899-907 |
|---|---|---|---|---|---|---|
| Pt. 1 | A24/2 | — | — | — | — | — |
| Pt. 2 | A24/33 | — | — | 0.13 | — | — |
| Pt. 3 | A24/2 | — | — | 0.14 | 0.06 | — |
| Pt. 4 | A2/11 | 0.05 | 0.16 | 0.06 | 0.05 | 0.05 |
| Pt. 5 | A24/31 | — | — | — | — | — |
| Pt. 6 | A2 | — | — | — | — | — |
| Pt 7 | A1/24 | 0.13 | — | — | — | — |
| Pt. 8 | A24 | — | — | 0.05 | — | — |
| Pt. 9 | A24/2 | — | — | 0.05 | — | — |
| Pt. 10 | A24/11 | — | — | 0.09 | — | — |
| Pt. 11 | A24/2 | — | — | — | — | — |
| Pt. 12 | A24/2 | — | — | 0.13 | — | — |
| Pt. 13 | A24 | — | — | 0.13 | — | — |
| HD1 | A24/33 | 0.08 | 0.09 | 0.08 | — | — |
| HD2 | A24/26 | — | 0.20 | 0.16 | 0.10 | — |
| HD3 | A2/26 | 0.22 | 1.50 | 0.20 | 0.18 | 0.34 |
| HD4 | A24/26 | — | — | 0.09 | — | — |
| HD5 | A2/24 | — | — | 0.08 | — | — |
| HD6 | A11/33 | — | — | — | — | — |
| HD7 | A2/24 | — | — | 0.05 | 0.05 | — |
| HD8 | A31/33 | — | — | — | — | — |
| HD9 | A2/24 | — | — | 0.19 | — | — |
| HD10 | A2/11 | — | — | 0.11 | — | — |
| HD11 | A2/24 | — | — | 0.18 | — | — |
| Anti-peptides Abs | Pt.(n = 13) | 2 | 1 | 8 | 2 | 1 |
| | HD (n = 11) | 2 | 3 | 9 | 3 | 1 |

| Subjects | EGFR124-13 | EGFR812-821 | EGFR625-633 | EGFR73-82 | EGFR54-62 | EGFR1015-1023 |
|---|---|---|---|---|---|---|
| Pt. 1 | — | — | — | — | 0.05 | — |
| Pt. 2 | 0.05 | — | — | — | 0.05 | — |
| Pt. 3 | 0.07 | — | — | — | 0.07 | — |
| Pt. 4 | 0.05 | 0.05 | 0.05 | — | 0.05 | 0.06 |
| Pt. 5 | — | — | — | — | — | — |
| Pt. 6 | — | — | — | — | — | — |
| Pt 7 | — | — | — | 0.06 | — | — |
| Pt. 8 | 0.49 | — | — | — | — | — |
| Pt. 9 | — | — | — | — | — | — |
| Pt. 10 | 0.13 | — | — | — | — | — |
| Pt. 11 | — | — | — | — | — | — |
| Pt. 12 | 0.08 | — | — | — | 0.09 | — |
| Pt. 13 | 0.12 | — | — | — | 0.14 | — |
| HD1 | — | — | — | — | — | — |
| HD2 | 0.10 | — | — | — | 0.06 | 0.05 |
| HD3 | 0.09 | 0.15 | 0.05 | — | 0.13 | 0.66 |
| HD4 | 0.05 | — | — | — | — | — |
| HD5 | — | — | — | — | — | — |
| HD6 | — | — | — | — | — | — |
| HD7 | — | — | — | — | — | — |
| HD8 | — | — | — | — | — | — |
| HD9 | — | — | — | — | — | — |
| HD10 | 0.05 | — | — | — | — | — |
| HD11 | 0.07 | — | — | — | 0.14 | — |
| Anti-peptides Abs | 7 | 1 | 1 | 1 | 6 | 1 |
| | 5 | 1 | 1 | 0 | 3 | 2 |

The OD values lower than the cut-off (0.04) were shown as —.

Significant levels of IgG reactive to the $EGFR_{800-809}$, $EGFR_{124-132}$, and $EGFR_{54-62}$ peptides (A value>0.04 at serum dilution of 1:100) were detected in sera of 8, 7, and 6 patients, respectively. Sera from 9, 5, and 3 out of 11 HDs tested also showed the significant levels of IgG reactive to $EGFR_{800-809}$, $EGFR_{124-132}$, and $EGFR_{54-62}$, respectively. In addition, significant levels of IgG reactive to the $EGF_{899-908}$, $EGFR_{1015-1023}$, $EGFR_{269-277}$, $EGFR_{899-907}$, $EGFR_{812-821}$, $EGFR_{625-633}$, $EGFR_{73-82}$, and $EGFR_{1015-1023}$ peptides were detected in sera from one or two cancer patients as well as a few HDs. The immune response to EGFR peptides observed in both cancer patients and HDs may not be surprising since EGFR is expressed not only in epithelial cancer cells but also in certain normal epithelial cells (References 1-3). Humoral responses to these EGFR peptides were observed in both HLA-A24 positive and -A24 negative subjects, although the majority of subjects were HLA-A24 positive. In contrast, significant levels of IgG reactive to the remaining 7 peptides were not detectable in any serum tested (data not shown).

These results indicate that, among the 18 synthetic peptides, $EGFR_{800-809}$, $EGFR_{124-132}$, and $EGFR_{54-62}$ are more preferable for induction of the immune response aimed by the present invention.

B. Evaluation of the Peptide Specificity of Anti-peptide Antibodies

The peptide specificity of anti-peptide IgG in the serum sample to each of the $EGF_{800-809}$, $EGFR_{124-132}$, and $EGF-R_{54-62}$ peptides was confirmed by an absorption test.

100 µl/well of serum samples (×100 dilution with 0.05% PBS) were absorbed with immobilized peptides (20 µg/well) in wells of plate for 2 h at 37° C. The absorption was repeated three times followed by testing of the anti-peptide IgG with ELISA.

Figure 3A:
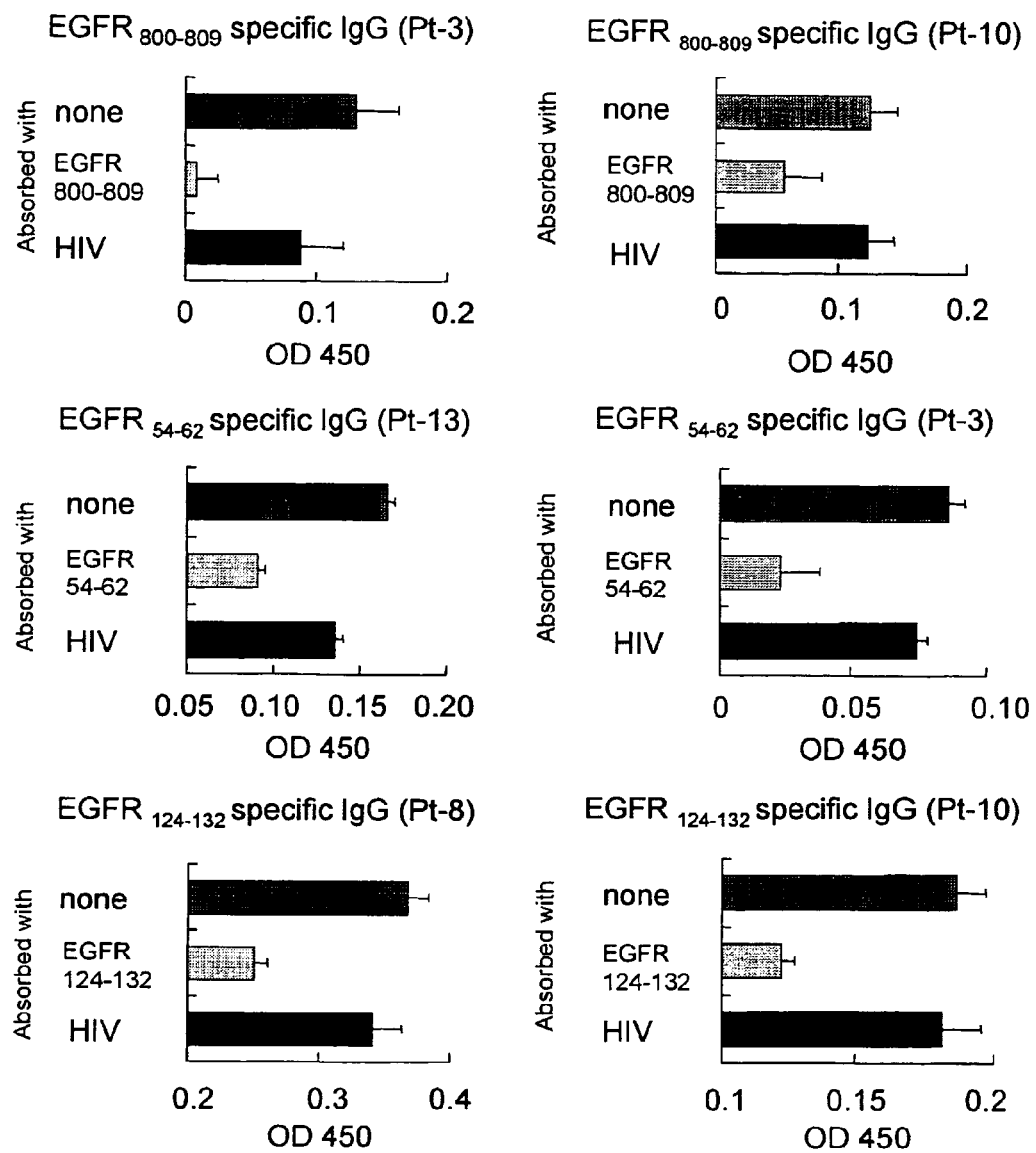
FIG. 3A shows the peptide specificity of the anti-peptide IgGs in the serum samples.

Representative results from sera of Pts. 2, 3, 8 and 10 are shown in FIG. 3A. The activities of these sera reactive to each of the three peptides were absorbed with the corresponding peptide, but not with the HIV peptide taken as a negative control (FIG. 3A).

Figure 3B:
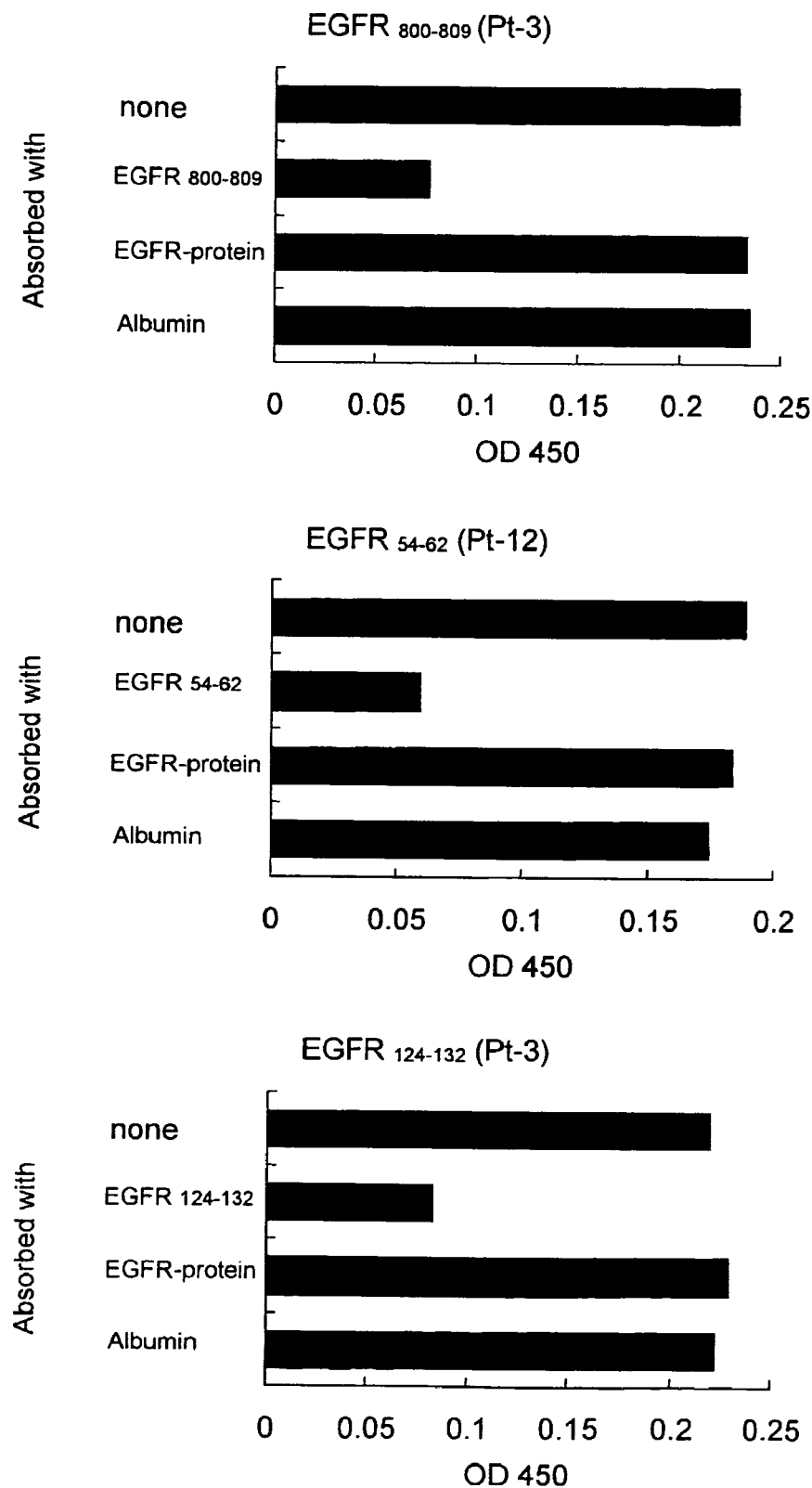
FIG. 3B shows the result of the assay for cross-reactivity of the anti-peptide IgGs to the whole EGFR protein.

To test whether the anti-peptide IgGs are reactive to the whole molecule of EGFR, patients' sera possessing anti-peptide activity were also absorbed with either immobilized EGFR isolated from human A431 cells with the purity of 85% (Upstate Charlottesville, USA) or immobilized human albumin as a negative control followed by measuring their anti-peptide activities by ELISA. Representative results from sera of Pts. 3 and 12 are shown in FIG. 3B. The level of the anti-peptide IgG reactive to any of the three peptides was not decreased at all by the absorption test (FIG. 3B), suggesting no cross-reactivity of the peptide IgG to the whole EGFR protein.

The results indicate that $EGFR_{800-809}$, $EGFR_{124-132}$, and $EGFR_{54-62}$ peptides of the invention can induce peptide specific humoral immune response.

Example 2

CTL Induction with EGFR-derived Peptides

A. IFN-γ Production $EGFR_{800-809}$, $EGFR_{124-132}$, and $EGFR_{54-62}$ peptides were tested for their ability to induce CTL in PBMCs of HLA-A24$^+$ NSCLC patients and HDs, utilizing IFN-γ production as an indicator of the induction.

For induction of peptide-specific CTLs, PBMCs ($15 \times 10^4$ cells/well) were incubated with 10 µM of each peptide in the four different wells of a 96-well microculture plate (Nunc, Roskilde, Denmark) in 200 µl culture medium containing IL-2, as reported previously. For peptide loading, C1R-A2402 cell line (HLA-2402 transfectant) was used (Reference 12). On the 14th day, the cells from each well were independently harvested and washed. These cells were divided into the four parts and each two of them were incubated for 18 h with C1R-A2402 cells pulsed in duplicate with a corresponding peptide or the negative control (HIV) peptide, and then the supernatants were collected for measurement of IFN-γ by ELISA. Background IFN-γ production in response to the HIV peptide (<50 pg/ml) was subtracted from the data. As a control for the ability to induce CTL activity, the two peptides ($EGFR_{43-51}$ and $EGFR_{943-952}$), to which IgG response was not detectable at all, were also tested.

Figure 4:
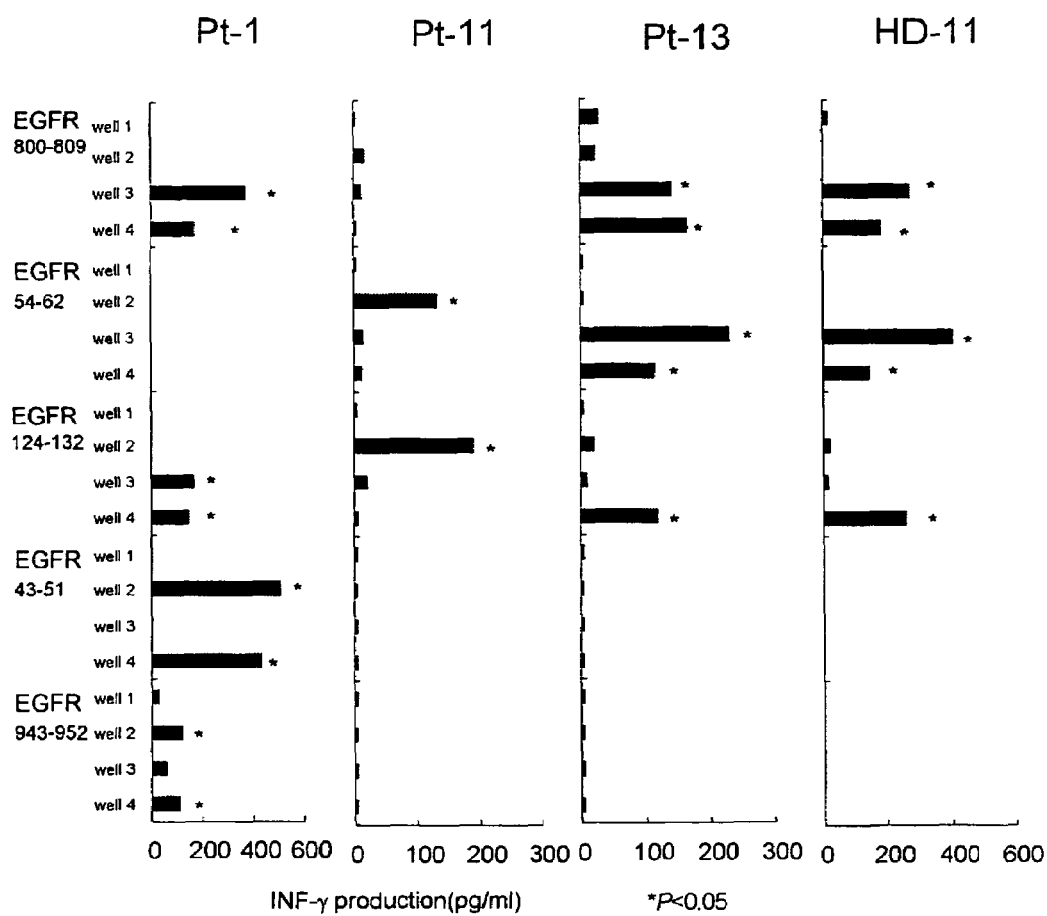
FIG. 4 shows the CTL induction by the EGFR-derived peptides. *P<0.05 (Student's t-test).

Representative results of the four cases (Pts. 1, 11, 13 and HD11) are shown in FIG. 4, in which the results from each of the four wells were provided.

The summary of all subjects is given in Table 2. The well of successful induction of peptide-specific CTLs was judged to be positive when the supernatant of well showed more than 100 pg/ml IFN-γ production with p-value of <at least 0.05. The mean values of the amount of IFN-γ of the positive wells among the 4 wells tested are shown in Table 2.

TABLE 2

Cellular responses to the EGFR peptides

Responses to the EGFR peptides (INF-γ production (pg/ml))

| Subjects | HLA | EGFR800-809 | EGFR54-62 | EGFR124-132 | EGFR43-51 | EGFR943-952 |
|---|---|---|---|---|---|---|
| Pt-1 | A24/2 | 376/172 | — | 168/150 | 509/432 | 126/115 |
| Pt-2 | A24/33 | — | — | 138 | — | — |
| Pt-3 | A24/2 | 430 | 154/170 | — | 160 | — |
| Pt-7 | A1/24 | 572 | 116 | — | — | 122/376 |
| Pt-10 | A24/11 | — | — | — | — | — |
| Pt-11 | A24/2 | — | 134 | 192 | — | — |
| Pt-12 | A24/2 | 122 | 202 | — | — | — |
| Pt-13 | A24 | 166/144 | 231/115 | 118 | — | — |
| HD-1 | A24/33 | — | 110/116 | 166 | 130 | — |
| HD-2 | A24/26 | 161/863/184 | 316/314 | 1375/724 | — | — |
| HD-4 | A24/26 | 164 | 132/116 | 176/206 | — | — |
| HD-5 | A2/24 | — | — | — | — | — |
| HD-11 | A2/24 | 280/190 | 410/150 | 267 | — | — |

(—) indicates when none of the 4 wells showed the positive response.

The $EGFR_{800-809}$, $EGFR_{54-62}$, and $EGFR_{124-132}$ peptides stimulated PBMCs in at least one of four wells to produce significant amounts of IFN-γ in response to C1R-A2402 cells pulsed with the corresponding peptide in 5, 5, and 4 of cancer patients tested, respectively. These peptides also stimulated to produce IFN-γ in 3, 4, and 4 of 5 HDs tested, respectively. The $EGFR_{43-51}$ and $EGFR_{943-952}$, to which IgG responses were not observed, also stimulated PBMCs to produce significant amounts of IFN-γ in response to C1R-A2402 cells pulsed with the corresponding peptide in 2 of 8 cancer patients tested, respectively (Table 2). The $EGFR_{43-51}$ or $EGFR_{943-952}$, stimulated PBMCs in 1 or 0 of 5 HDs tested.

These results indicate that $EGFR_{800-809}$, $EGFR_{124-132}$, and $EGFR_{54-62}$, and are capable of inducing CTLs.

B. Anti-tumor Cytotoxic Activity

The cytotoxicity of the peptide-stimulated PBMCs was evaluated by a 6 h $^{51}$Cr-release assay to confirm the CTL induction.

Expression of EGFR on tumor cell lines was tested by flowcytometoric assay with immunofluorescence-labeled anti-EGFR monoclonal antibody (mAb) (Santa Cruz Biotechnology, Santa Cruz, Calif.) (Reference 13). A431 tumor cells and Phytohemagglutinin (PHA)-blastoid T cells were used as a positive and negative control, respectively. The representative results of histograms were shown in FIG. 1. Based on these results, the following tumor cell lines were used as target cells in the 6 hr-$^{51}$Cr-release assay in this study; 11-18 (HLA-A24/2, human lung adenocarcinoma, $EGFR^+$), QG56 (HLA-A26, lung squamous cell carcinoma (SCC), $EGFR^+$), Sq-1 (HLA-A24/11, lung SCC, $EGFR^±$), LC65A (HLA-A24/11, non-small cell lung carcinoma, $EGFR^+$), SKOV3 (HLA-A3/28, ovarian cancer, $EGFR^+$) and SKOV3-A24 (HLA-A24-transfected SKOV3). PHA-blastoid T cells from PBMCs were used as a negative control of target cells for the 51Cr-release assay.

The cells producing IFN-γ in response to the corresponding peptide in the assay described above (A) were collected from the wells and further cultured with IL-2 alone for 10-14 days to obtain a large number of cells for the 6 h $^{51}$Cr-release assay. The standard 6-h $^{51}$Cr-release assay was performed at three E/T (effecter cells/target cells) ratios. This method was reported previously (Reference 12). Two-tailed Student's-t test was employed for the statistical analysis.

Figure 5:
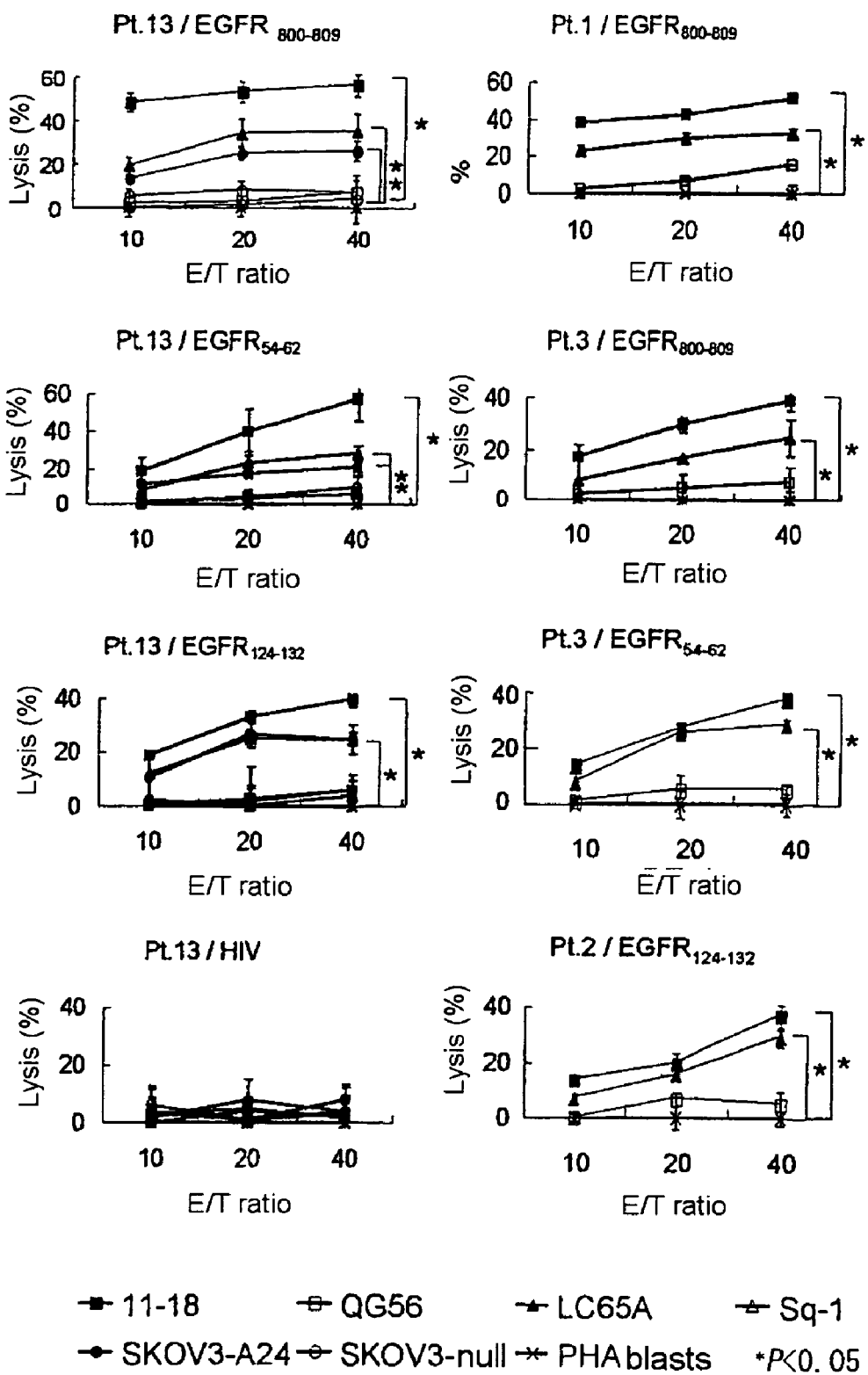
FIG. 5 shows the cytotoxic activity of peptide-stimulated PBMCs against tumor cell lines. *P<0.05 (Two-tailed student's t-test).

The representative results of the 4 patients (Pts. 1, 2, 3, and 13) are shown in FIG. 5. The values represent the mean ±SD of specific lysis (%). These peptide-stimulated PBMCs showed significant levels of cytotoxicity against all of the 11-18 NSCLC cells (HLA-A24$^+$, EGFR$^+$), LC65A non-small cell lung carcinoma cells (HLA-A24$^+$, EGFR$^+$), and SKOV3-A24 tumor cells (HLA-A24$^+$, EGFR$^+$), but failed to kill any of the QG56 NSCLC cells (HLA-A24$^-$, EGFR$^+$), Sq-1 NSCLC cells (HLA-A24$^+$, EGFR$^+$) and SKV3 tumor cells (HLA-A24$^-$, EGFR$^+$) tested. These PBMCs also failed to kill PHA-blastoid T cells (HLA-A24$^+$, EGFR$^-$). PBMCs stimulated with the HIV peptide, taken as a negative control, did not show the HLA-A24-restricted cytotoxicity (FIG. 5, the lowest left column). Those results suggest that the PBMCs possess HLA-24-restricted cytotoxicity reactive to EGFR$^+$ tumor cells.

Furthermore, the HLA-restricted and peptide-specific cytotoxicity were confirmed by the inhibition and competition assays, respectively.

For the inhibition assay, 20 μg/ml of anti-HLA-class I (W6/32, IgG2a), anti-HLA-class II (H-DR-1, IgG2a), anti-CD8 (Nu-Ts/c, IgG2a), anti-CD4 (Nu-Th/i, IgG1), and anti-CD14 (JML-H14, IgG2a) (as a negative control) mAbs were used. For the competition assay to study the peptide specific cytotoxicity, unlabeled C1R-2402 cells pulsed with the corresponding peptide or the HIV peptide as a negative control were added to the $^{51}$Cr-release assay at a cold to hot target cell ratio of 10 to 1. The values represent the mean ±SD of specific lysis (%), and two-tailed Student's-t test was employed for the statistical analysis.

Figure 6:
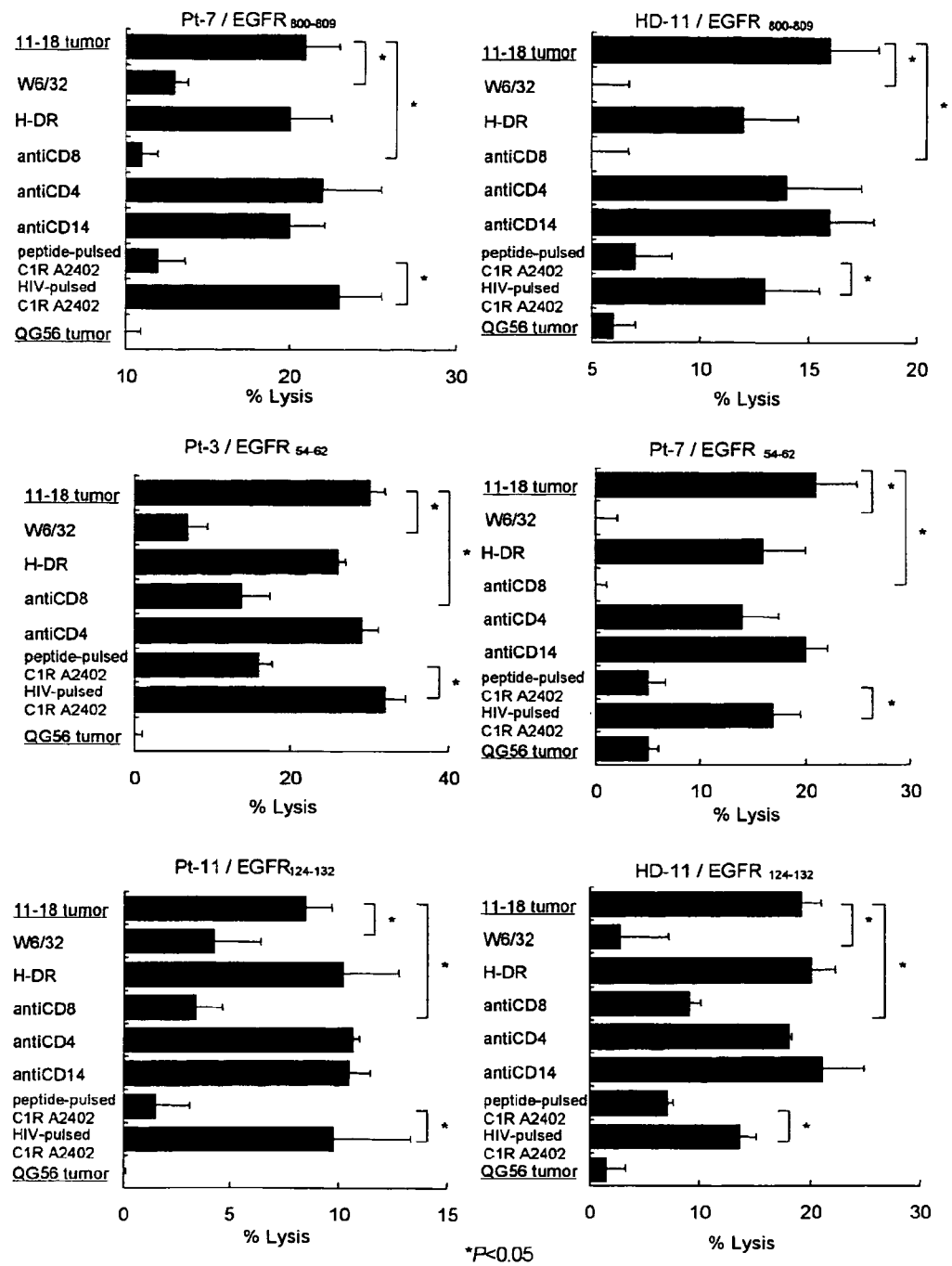
FIG. 6 shows HLA-restricted and peptide specific cytotoxicity demonstrated by the inhibition assay and the competition assay.
Figure 7:
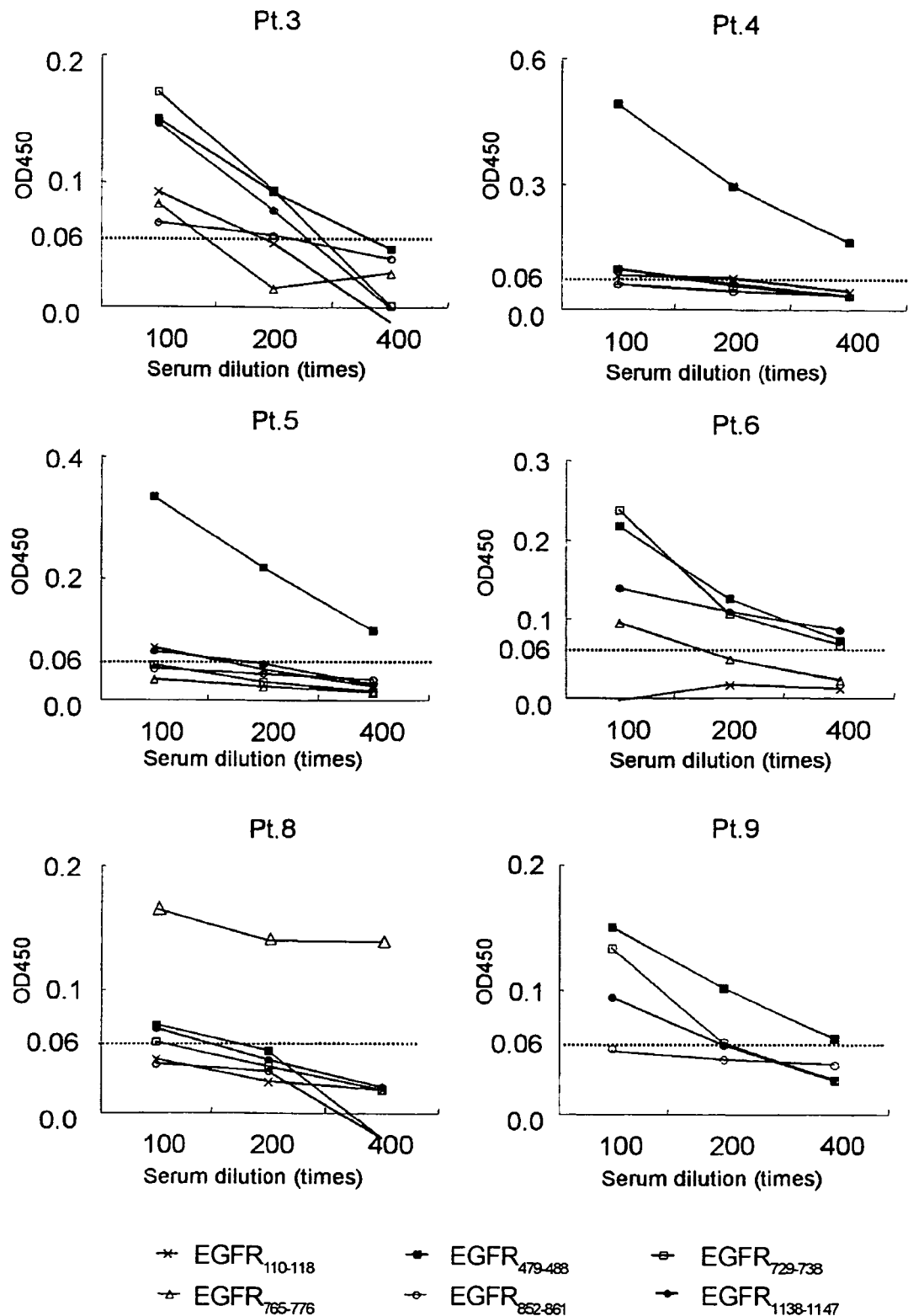
FIG. 7 shows the detection of anti-peptide IgGs in the serum samples.
Figure 8:
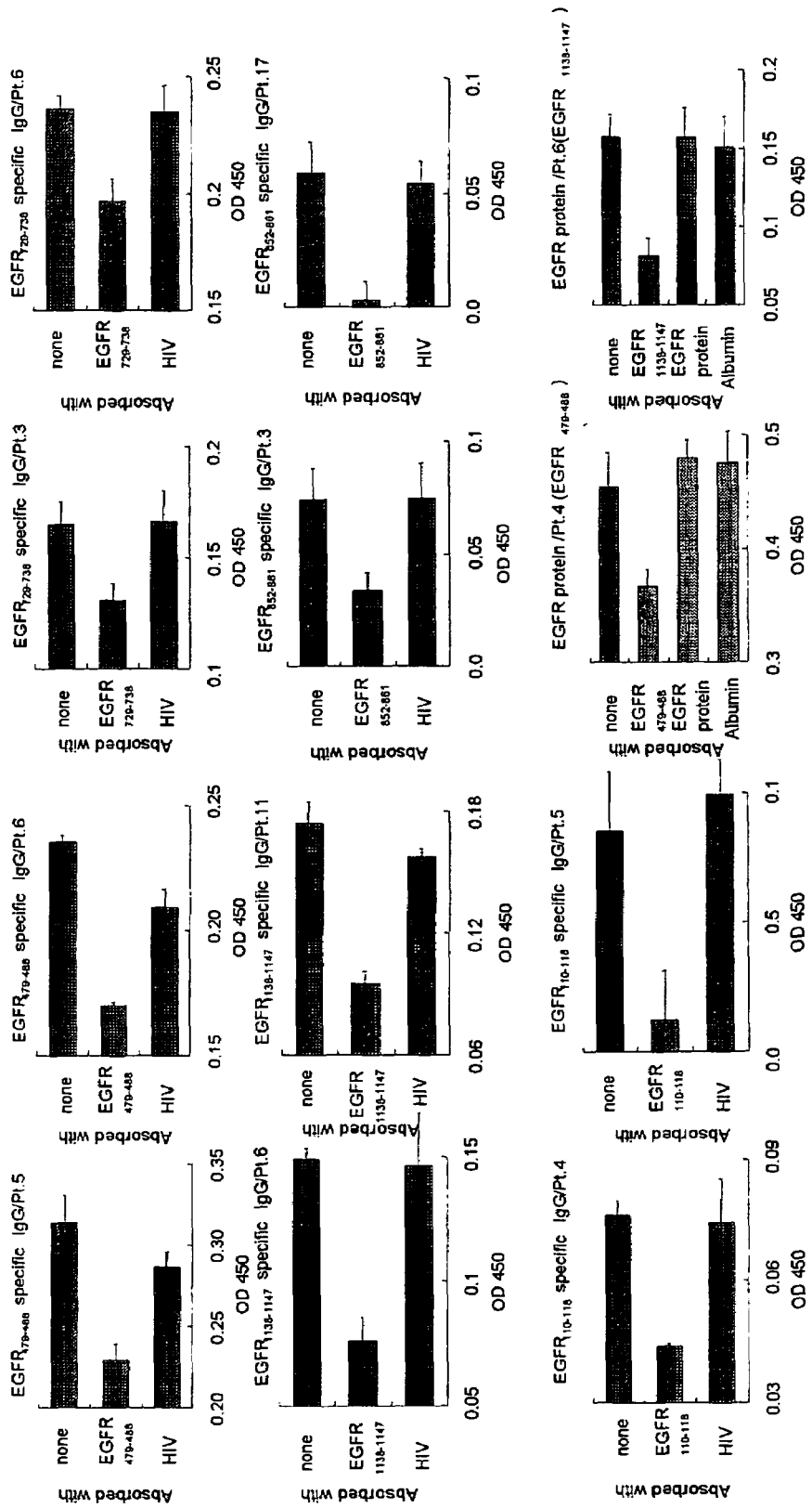
FIG. 8 shows the peptide specificity of the anti-peptide IgGs in the serum samples.
Figure 9:
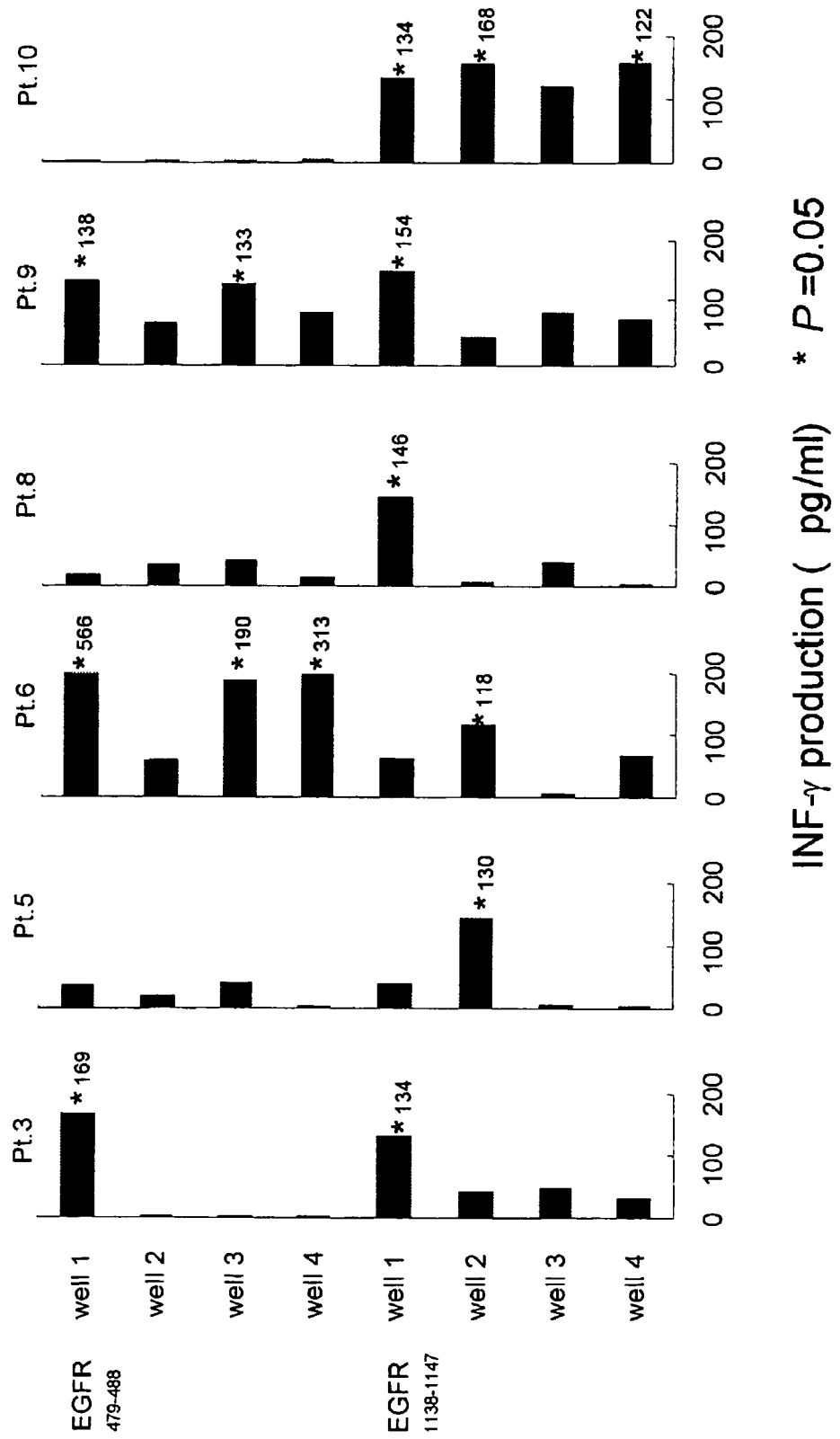
FIG. 9 shows the CTL induction by the EGFR-derived peptides. PBMCs derived from HLA-A2$^+$ cancer patients were stimulated with any of the peptides and their IFN-γ production against T2 cells (HLA-A2, T-B hybridoma) pulsed with the corresponding peptide were determined. *P<0.05 (Student's t test).
Figure 10:
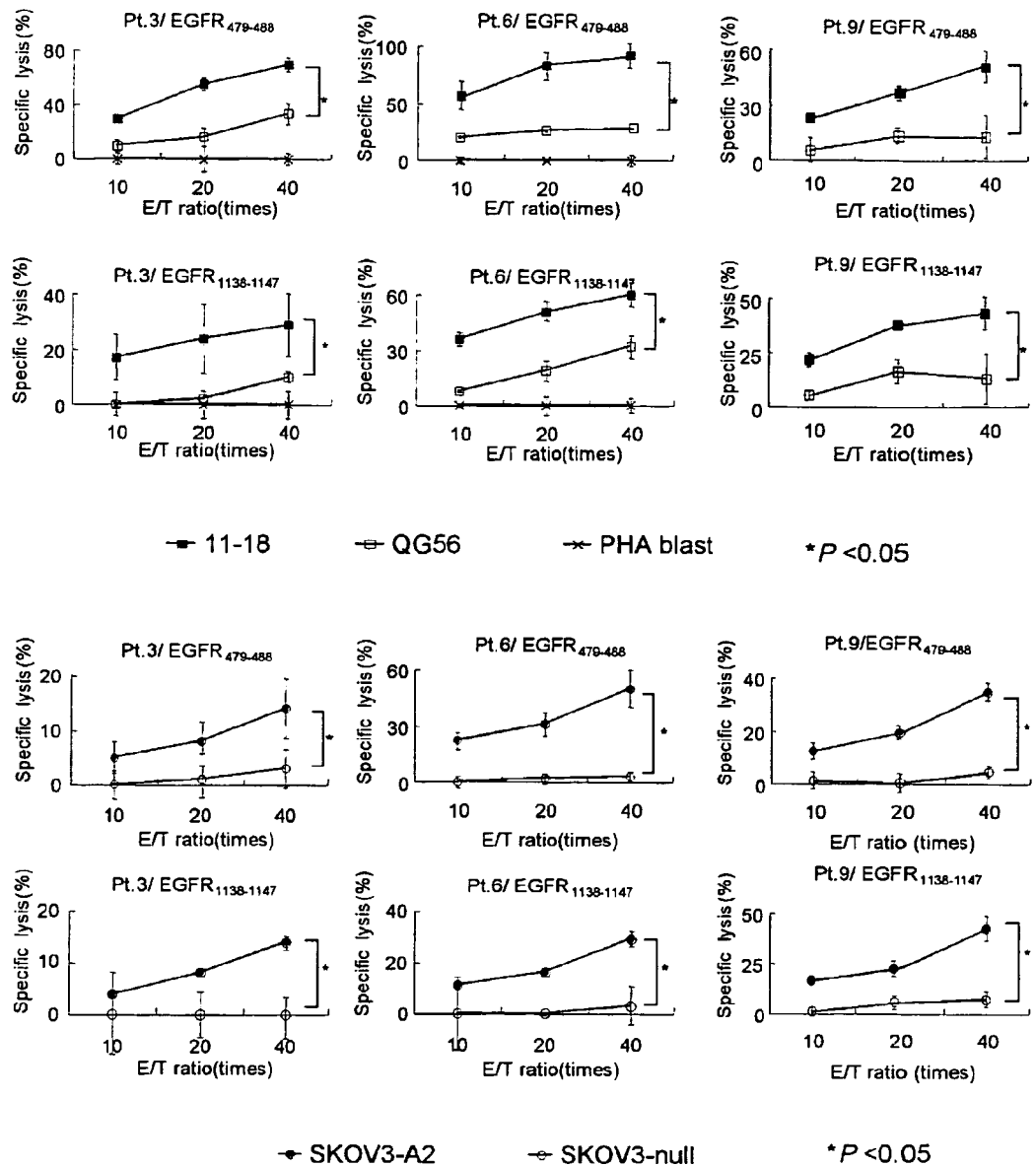
FIG. 10 shows the cytotoxic activity of peptide-stimulated PBMCs against tumor cell lines. SKOV3-A2 (HLA-A2$^+$, EGFR$^+$) and SKOV3 (HLA-A2$^-$, EGFR$^+$) were used as the tumor cell lines. *P<0.05 (Two-tailed student's t-test).
Figure 11:
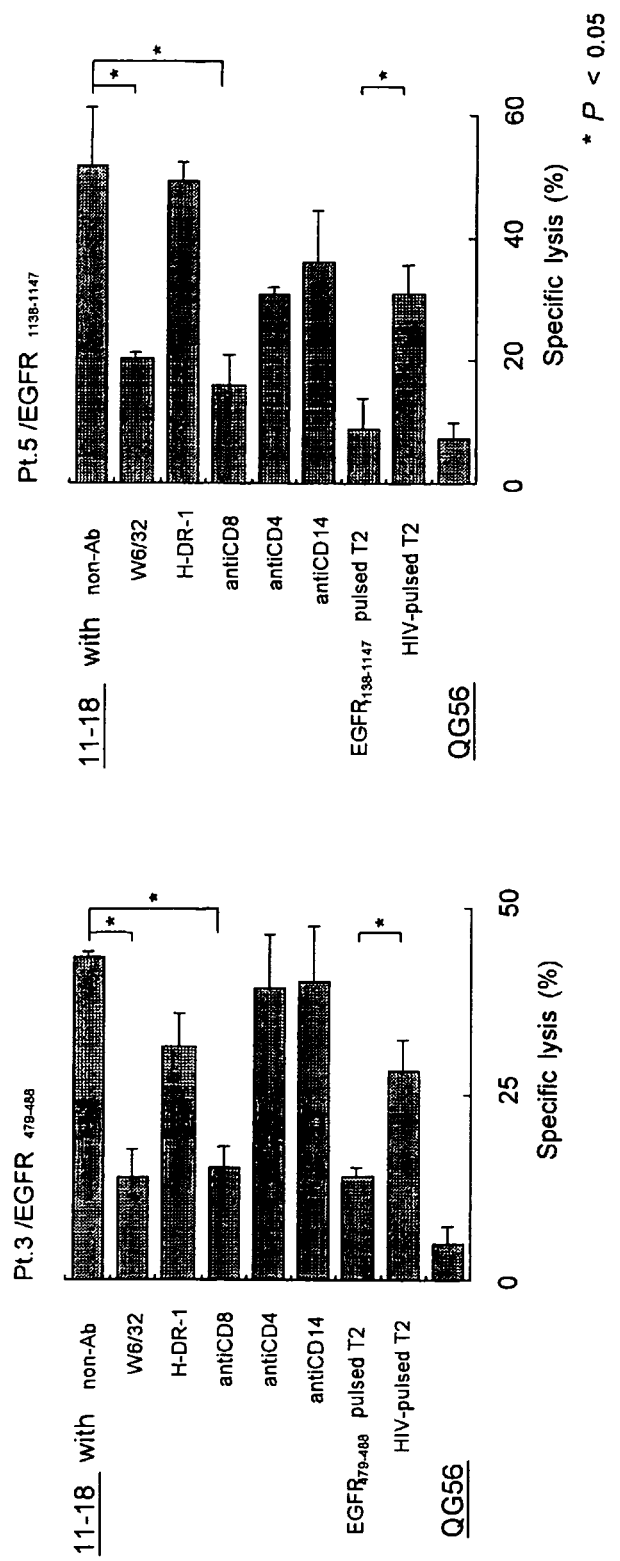
FIG. 11 shows HLA-restricted and peptide specific cytotoxicity demonstrated by the inhibition assay and the competition assay. Peptide-pulsed T2 cells were used for the competition assay.

The cytotoxicities of these peptide-stimulated PBMCs were significantly inhibited by anti-class I (W6/32) or anti-CD8 mAb, but not by the other mAb in the assay. The cytotoxicities were also inhibited by addition of the corresponding peptide-pulsed C1R-A2402 cells, but not by the HIV peptide-pulsed cells (FIG. 6).

These results suggest that the CTL activities induced by $EGFR_{800-809}$, $EGFR_{124-132}$, and $EGFR_{54-62}$ peptides were largely mediated by the peptide-reactive CD8$^+$ T cells with an HLA-class I-restricted manner.

Example 3

In a similar way to Examples 1 and 2, $EGFR_{479-488}$ and $EGFR_{1138-1147}$ were identified to be capable of inducing humoral immune response and HLA-A2-restricted cytotoxic immune response. The results were shown in Table 3 and FIG. 7 to 11.

TABLE 3

Humoral responses to the peptides
Responses to the EGFR peptides (OD values)

| Subjects | HLA | Subtype | EGFR10-18 | EGFR61-70 | EGFR110-118 | EGFR479-488 | EGFR599-607 |
|---|---|---|---|---|---|---|---|
| Pt. 1 | A2/24 | A0207 | —² | — | — | — | — |
| Pt. 2 | A2/24 | A0206 | — | — | — | — | — |
| Pt. 3 | A2/24 | A0206 | — | — | 0.09 | 0.15 | — |
| Pt. 4 | A2/11 | A0206 | 0.26 | — | 0.08 | 0.49 | — |
| Pt. 5 | A2 | A0201 | — | — | 0.09 | 0.33 | — |
| Pt. 6 | A2/24 | A0206 | — | — | — | 0.22 | — |
| Pt. 7 | A2/3 | A0201 | — | — | — | — | — |
| Pt. 8 | A2/24 | A0206 | — | — | — | 0.07 | — |
| Pt. 9 | A2/24 | A0201 | — | — | — | 0.15 | — |
| Pt. 10 | A2 | A0207 | — | 0.07 | 0.14 | 0.12 | 0.13 |
| Pt. 11 | A24/33 | | — | 0.07 | — | 0.10 | 0.17 |
| Pt. 12 | A24 | | — | — | — | 0.21 | 0.08 |
| Pt. 13 | A24 | | — | — | — | — | 0.07 |
| Pt. 14 | A24 | | — | — | — | — | — |
| Pt. 15 | A24 | | — | — | — | 0.55 | — |

TABLE 3-continued

Humoral responses to the peptides
Responses to the EGFR peptides (OD values)

| | | | | | | | |
|---|---|---|---|---|---|---|---|
| Pt. 16 | A24 | | — | — | — | 0.17 | — |
| Pt. 17 | A24/31 | | — | — | — | 0.24 | — |
| Pt. 18 | A24 | | — | — | — | 0.07 | — |
| Pt. 19 | A24/33 | | — | — | — | — | — |
| Pt. 20 | A24/11 | | — | — | — | — | — |
| HD1 | A2/24 | A0206 | — | — | — | — | 0.20 |
| HD2 | A2/24 | A0206 | — | — | — | — | 0.09 |
| HD3 | A2/11 | A0206 | — | — | — | 0.26 | — |
| HD4 | A2/26 | A0201 | — | — | — | 0.13 | — |
| HD5 | A2 | A0206 | — | — | — | — | — |
| HD6 | A2/24 | A0201 | — | — | — | — | — |
| HD7 | A24/33 | | — | — | — | — | — |
| HD8 | A24/26 | | — | — | — | — | — |
| HD9 | A24/26 | | 0.07 | 0.07 | — | — | 0.20 |
| HD10 | A24 | | — | — | — | — | — |
| HD11 | A11/33 | | — | 0.09 | 0.09 | — | 0.13 |
| Anti-peptide Abs | Pt (n = 20) | | 1 | 2 | 4 | 13 | 4 |
| | HD(n = 11) | | 1 | 2 | 1 | 2 | 4 |

| Subjects | HLA | EGFR653-662 | EGFR654-662 | EGFR729-738 | EGFR765-776 | EGFR852-861 | EGFR1138-1147 |
|---|---|---|---|---|---|---|---|
| Pt. 1 | A2/24 | — | — | — | — | — | — |
| Pt. 2 | A2/24 | — | — | — | — | — | — |
| Pt. 3 | A2/24 | — | — | 0.17 | 0.08 | 0.07 | 0.15 |
| Pt. 4 | A2/11 | — | — | 0.10 | — | — | 0.10 |
| Pt. 5 | A2 | — | — | — | — | — | 0.08 |
| Pt. 6 | A2/24 | — | — | 0.24 | 0.10 | — | 0.14 |
| Pt. 7 | A2/3 | — | — | — | — | — | — |
| Pt. 8 | A2/24 | — | — | — | 0.16 | — | 0.07 |
| Pt. 9 | A2/24 | — | — | 0.13 | — | — | 0.09 |
| Pt. 10 | A2 | 0.07 | — | 0.07 | — | — | 0.13 |
| Pt. 11 | A24/33 | — | 0.09 | 0.17 | — | — | 0.16 |
| Pt. 12 | A24 | — | — | — | — | — | 0.07 |
| Pt. 13 | A24 | — | — | — | — | — | — |
| Pt. 14 | A24 | — | — | — | 0.18 | — | — |
| Pt. 15 | A24 | — | — | 0.59 | — | — | — |
| Pt. 16 | A24 | — | — | — | — | — | — |
| Pt. 17 | A24/31 | — | — | 0.10 | — | 0.07 | 0.10 |
| Pt. 18 | A24 | — | — | — | — | — | — |
| Pt. 19 | A24/33 | 1.22 | — | 0.31 | — | — | — |
| Pt. 20 | A24/11 | — | — | 0.30 | — | — | — |
| HD1 | A2/24 | — | 0.07 | — | — | — | 0.13 |
| HD2 | A2/24 | — | — | — | — | — | — |
| HD3 | A2/11 | — | — | — | — | — | — |
| HD4 | A2/26 | — | — | — | — | — | 0.08 |
| HD5 | A2 | — | — | — | — | — | — |
| HD6 | A2/24 | — | — | — | — | — | — |
| HD7 | A24/33 | — | — | — | — | — | — |
| HD8 | A24/26 | — | — | — | — | — | — |
| HD9 | A24/26 | — | 0.12 | — | — | — | 0.26 |
| HD10 | A24 | — | — | — | — | — | 0.17 |
| HD11 | A11/33 | — | 0.07 | — | — | — | 0.15 |
| Anti-peptide Abs | | 2 | 1 | 10 | 4 | 2 | 10 |
| | | 0 | 3 | 0 | 0 | 0 | 5 |

The OD values lower than the cut-off (0.06) were shown as —.

The above results indicate that EGFR-derived peptides of the present invention are useful as cancer vaccines in EGFR-based immunotherapy.

INDUSTRIAL APPLICABILITY $EGFR_{800-809}$, $EGFR_{124-132}$, $EGFR_{54-62}$, $EGFR_{479-488}$, and $EGFR_{1138-1147}$ of the invention have the ability to elicit both cellular and humoral immune responses, suggesting the higher immunogenicity of them as compared to previous HER2/neu-derived CTL epitope peptides (References 6-9).

Although only a part of NSCLC patients respond to a tyrosine kinase inhibitor ZD1839, there is no suitable laboratory marker to predict the clinical response to it. It has been observed that the level of immune response to the EGFR peptides of the invention correlates to the clinical response to ZD1839, and therefore the EGFR peptides of the invention may be useful in the prediction of the clinical response to ZD1839 (References 4, 5).

HLA-A24 allele was found in 60% of Japanese (with 95% of these cases being genotypically HLA-A2402), in 20% of Caucasians, and 12% in Africans (Reference 18). These findings may provide a new insight for development of the EGFR-based immunotherapy for substantial numbers of NSCLC patients in the world.

What is claimed is:

1. A peptide selected from the group consisting of EGFR$_{800-809}$ (SEQ ID NO: 1), EGFR$_{124-132}$ (SEQ ID NO: 2), EGFR$_{54-62}$ (SEQ ID NO: 3), EGFR$_{479-488}$ (SEQ ID NO: 4) or EGFR$_{1138-1147}$ (SEQ ID NO: 5).

2. A pharmaceutical composition comprising the peptide of claim 1, for inducing a cytotoxic T lymphocytes and an antibody specific for said peptide.

* * * * *